United States Patent [19]
Boger

[11] Patent Number: 5,939,268
[45] Date of Patent: Aug. 17, 1999

[54] COMBINATORIAL LIBRARIES OF MOLECULES AND METHODS FOR PRODUCING SAME

[75] Inventor: Dale L. Boger, La Jolla, Calif.

[73] Assignee: The Scripps Research Institute, La Jolla, Calif.

[21] Appl. No.: 08/281,196

[22] Filed: Jul. 26, 1994

[51] Int. Cl.$^6$ .......................... G01N 33/53; G01N 33/543
[52] U.S. Cl. ........................... 435/7.1; 436/518; 549/498; 549/499; 544/224; 548/470; 548/482; 548/573; 546/181
[58] Field of Search ............................. 546/181; 548/470, 548/482, 573; 544/224; 549/498, 499; 436/518; 435/7.1

[56] References Cited

U.S. PATENT DOCUMENTS

| | | | |
|---|---|---|---|
| 4,173,646 | 11/1979 | Shepard et al. | 424/270 |
| 4,554,106 | 11/1985 | DeLuca et al. | 260/397.2 |
| 4,863,931 | 9/1989 | Schumacher et al. | 514/290 |
| 5,182,366 | 1/1993 | Huebner et al. | 530/334 |
| 5,288,514 | 2/1994 | Ellman | 427/2 |
| 5,405,830 | 4/1995 | Rendina et al. | 504/298 |

FOREIGN PATENT DOCUMENTS

| | | |
|---|---|---|
| 9119818 | 12/1991 | WIPO . |
| 9200091 | 1/1992 | WIPO . |
| 9209300 | 6/1992 | WIPO . |
| 9306121 | 4/1993 | WIPO . |
| 9309668 | 5/1993 | WIPO . |
| WO 94 06451 | 3/1994 | WIPO . |
| WO 94 08051 | 4/1994 | WIPO . |

OTHER PUBLICATIONS

Geysen, et al., Use of peptide synthesis to probe viral antigens for epitopes to a resolution of a single amino acid, *Proc. Natl. Acad. Sci. USA,* vol. 81, pp. 3998–4002, Jul. 1984.

Lam et al., A new type of synthetic peptide library for indentifying ligand–binding activity, Nature, vol. 354, Nov. 7, 1991, pp. 82–84.

Houghten et al., Generation and use of synthetic peptide combinatorial libraries for basic research and drug discovery, Nature, vol. 354, Nov. 7, 1991, pp. 84–86.

*Journal of the American Chemical Society*, vol. 116, No. 14, pp. 6101–6106, (Jul. 13, 1994) G. MacBeath et a., Monitoring Catalytis Activity by Immunoassay: Implications for Screening (See whole document).

*Journal of the Chemical Society*, Perkin Transactions No. 1, No. 11 pp. 1399–1406 (1992) Z. Xhou et al., Double Ring Closure of Diacetylenic Compounds With Activated Olefins in the Presence of a Cobalt (0) Catalyst, p. 1404, Figure 7A.

*Primary Examiner*—Matthew V. Grumbling
*Attorney, Agent, or Firm*—Thomas E. Northrup

[57] ABSTRACT

This invention features methods of synthesizing combinatorial libraries of chemical compounds, and combinatorial libraries of chemical compounds formed by the methods of this invention. Specifically, Diels-Alder chemistry is utilized to generate libraries of diverse molecules which are easily differentially functionalized with various chemical moities and in one aspect are configured to act as non-hydrolyzable peptidomimetics.

15 Claims, 17 Drawing Sheets

EXAMPLE

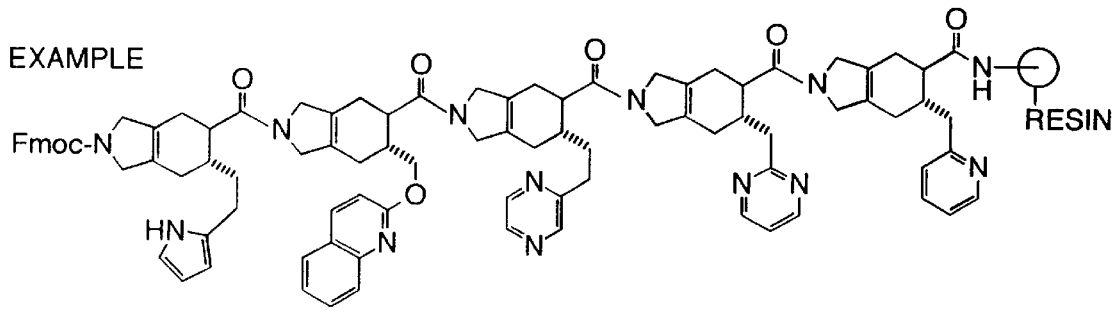

DESIGN CONSIDERATIONS:
- REPETITIVE AMIDE COUPLING
    HIGH YIELD, EASILY ACCESSIBLE REAGENTS
    EFFICIENCY OF COUPLING MAY BE ASSESSED BY ASSAY OF
    LIBERATED $C_6F_5OH$
- VARIABLE DIENOPHILE
    READILY ACCESSIBLE THROUGH HORNER-EMMONS OR WITTIG
      REACTION FROM CORRESPONDING ALDEHYDE
    GOOD REACTIVITY FOR DIELS-ALDER REACTION
    TRANS OLEFIN STEREOCHEMISTRY ACCESSIBLE IN SYNTHESIS
      TRANSLATES INTO CLEAN TRANS PRODUCT (ONE ISOMERS)
    HIGH YIELD AMIDE COUPLING OF DIENOPHILE ACTIVE ESTERS
    VARIABLE LINKER X PROVIDES ADDITIONAL DIVERSITY FOR ACCESSIBLE
      RELATIONSHIPS OF $R^1$- $R^2$ CHOICE OF VARIABLE R IS UNLIMITED
- DIENE
    COMMON, SINGLE REAGENT USED REPETITIVELY IN EACH CYCLE
    REACTIVITY: HIGH REACTIVITY DUE TO:
        STRAIN
        CONSTRAINED CISOID DIENE CONFORMATION
    REGIOCHEM: SYMMETRICAL DIENE ENSURES SINGLE DIELS-ALDER
            REGIOISOMER
    STEREOCHEM: 2,3-DISUBSTITUTED DIENE ENSURES NO
      ADDITIONAL/UNCONTROLLED PRODUCT STEREOCHEM.
- Fmoc PROTECTING GROUP
    COMPATIBLE WITH OLIGO/AMIDE/DIELS-ALDER CHEMISTRY
    UV ASSAY OF DEPROTECTION FOR ASSESSING DIELS-ALDER
    CYCLE EFFICIENCY

FIG. 2

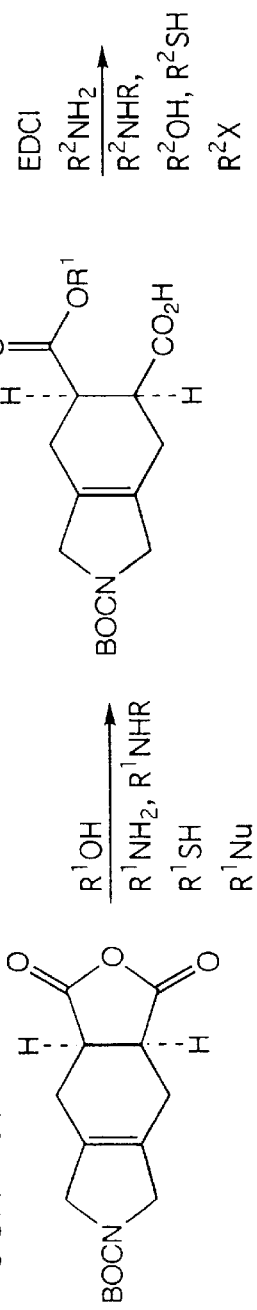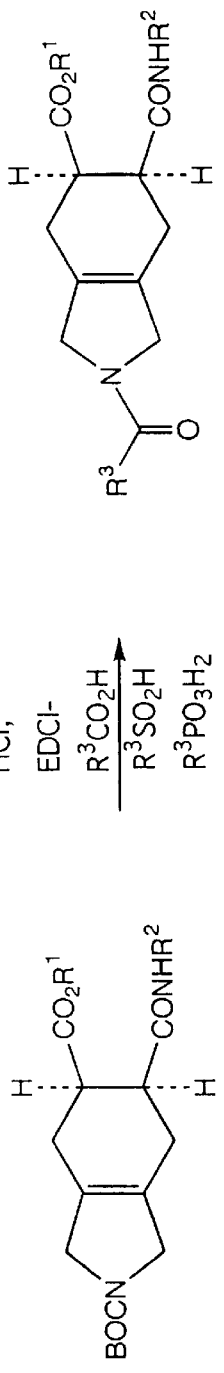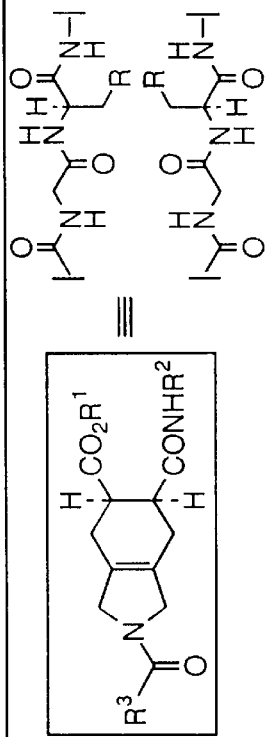
FIG. 4a-1

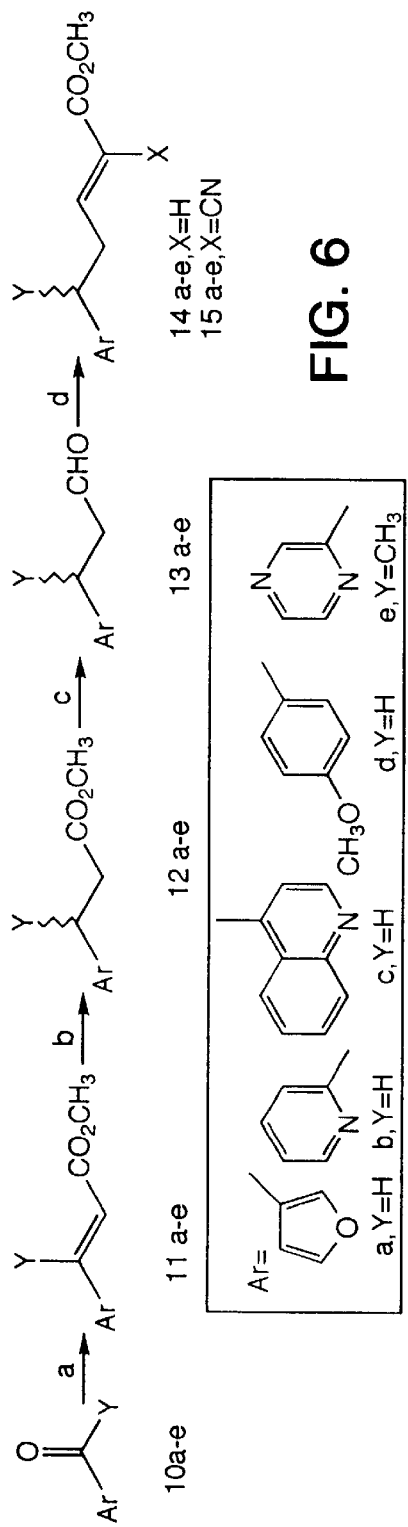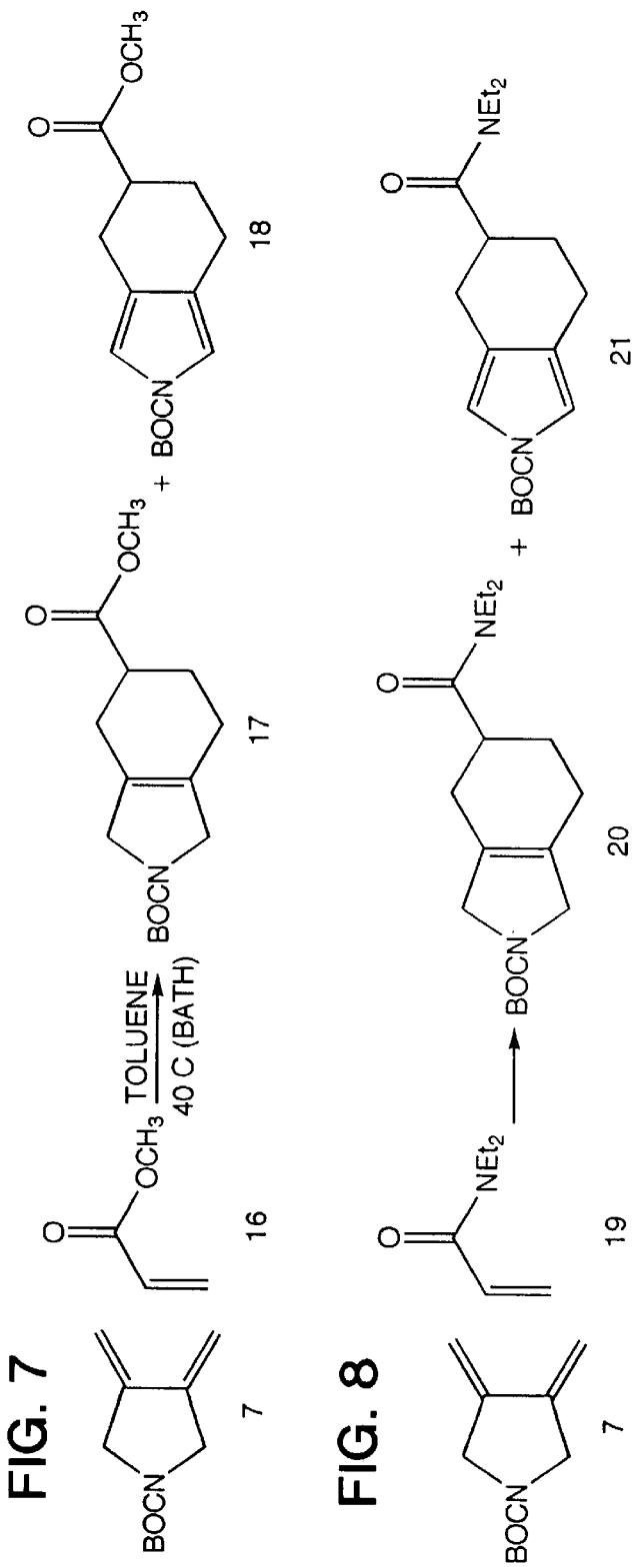
FIG. 6
FIG. 7
FIG. 8

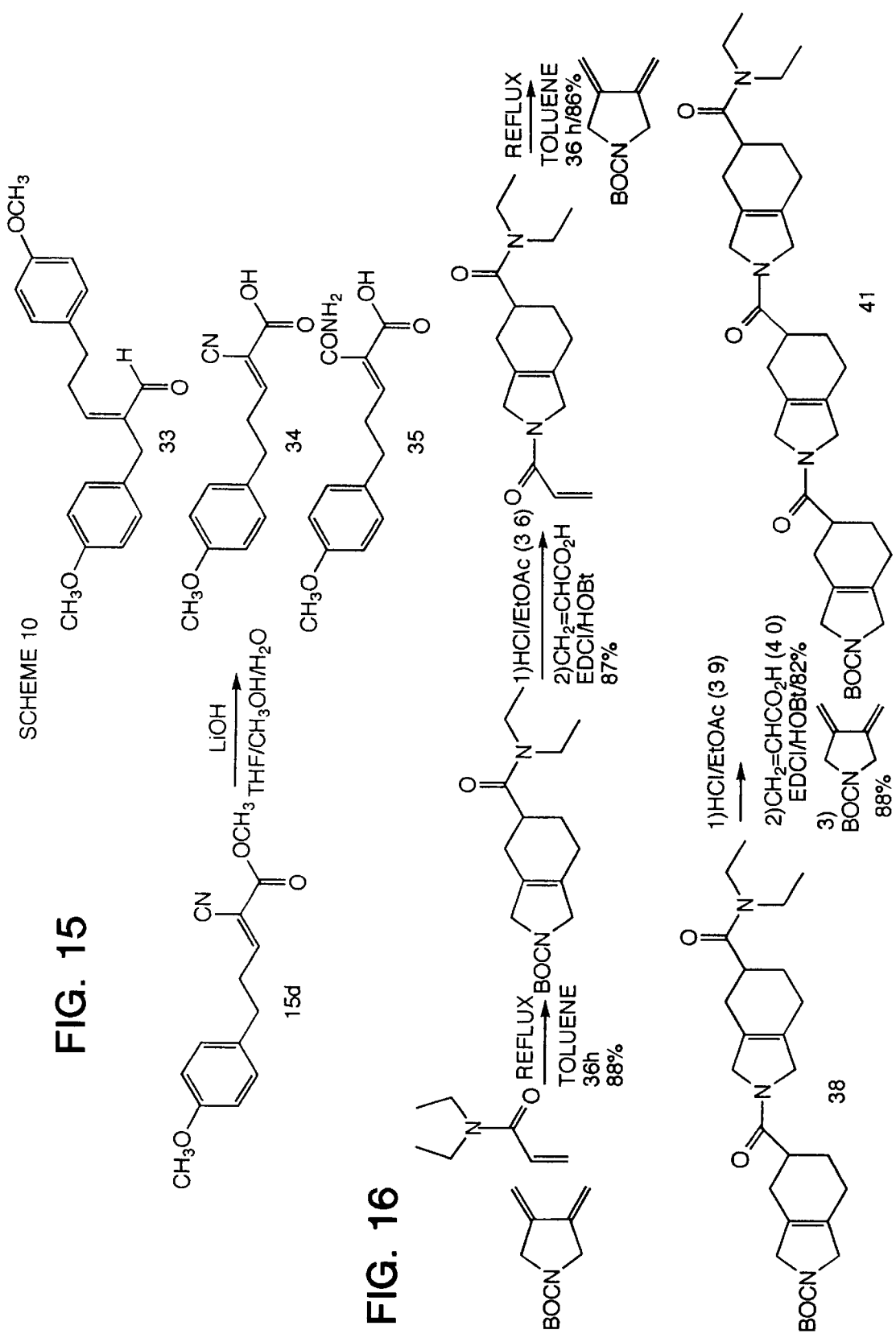

a b c d e f g h

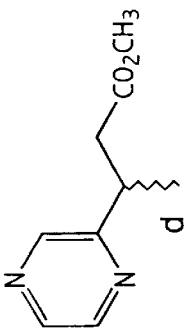
FIG. 18a
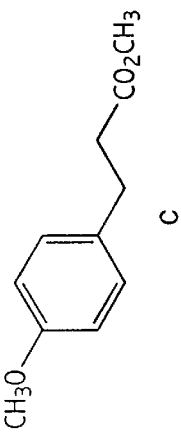
FIG. 18b
FIG. 18c
FIG. 18d
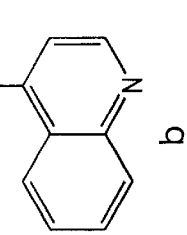
FIG. 18e
FIG. 18f
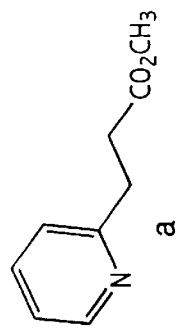
FIG. 18g
FIG. 18h
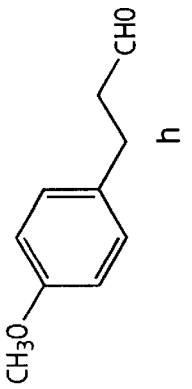
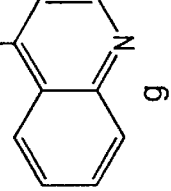
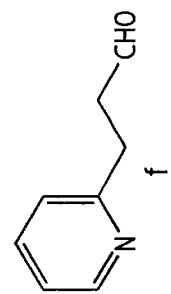
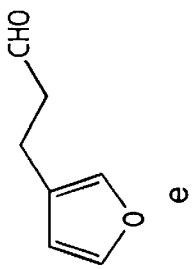

a b c d e f g h

DIENE + DIENOPHILE → ADDUCT 5,939,268

COMBINATORIAL LIBRARIES OF MOLECULES AND METHODS FOR PRODUCING SAME

BACKGROUND OF THE INVENTION

This invention relates to combinatorial libraries and methods for their generation.

The rapid production of diverse collections or libraries of chemical compounds is an important goal for those desiring to screen large numbers of novel compounds or diversomers for pharmacological activity. Combinatorial synthesis has been utilized to create libraries of molecules. These libraries often consist of oligomeric or polymeric molecules created from the sequential addition of monomeric subunits. However, typically the monomer subunits utilized have been amino acids, nucleic acid bases or carbohydrates. The reactions used to couple the subunits are standard reactions such as dehydration synthesis reactions.

The initial report of rapid concurrent solid phase synthesis by Geysen and co-workers, Geysen, H. M.; Meleon, R. H.; Barteling, S. J., *Proc. Natl. Acad. Sci. USA*, Vol. 81, p. 3998 (1984), described the construction of multi-amino acid peptide libraries. Houghten et al., 354 *Nature* 84, 1991 and WO 92/09300 (PCT/US91/08694), describe the generation and use of synthetic peptide combinatorial libraries for basic research and drug discovery. These libraries are composed of mixtures of free peptides which form a heterogenous library. Systematic identification of optimal peptide ligands is achieved by screening a library followed by iterative selection and synthesis processes. For example, one library consisted of a series of six residue peptides having the first two positions specifically defined, and the last four positions consisting of a random mixture of 18 L-amino acids. This library was screened to determine which pair of defined peptides had optimum activity in an assay. A second library was then synthesized in which the optimal pair of peptides were included, the third position of each peptide individually synthesized, and the last three peptides consisted of a random mixture of 18 L-amino acids. This library was screened as before and the process repeated until the optimum six residue peptide was identified. Houghten et al. state:

"A number of other libraries, such as one composed entirely of D-amino acids, have been prepared which in total permit the systematic screening of hundreds of millions of peptides.

A fundamental feature of SPCLs [synthetic peptide combinatorial libraries] is that free peptides can be generated and used in solution in virtually all existing assay systems at a concentration of each peptide most applicable to the assay. This approach has also been successfully used in radioreceptor assays (opioid peptides) and plaque inhibition assays (human immunodeficiency virus (HIV-1) and Herpes Simplex Virus (HSV)). SPCLs, as described, greatly aid all areas of drug discovery and research involving peptides."

Lam et al., 354 *Nature* 82, 1991, and WO 92/00091 (PCT/US91/04666) and Houghten et al., 354 *Nature* 84, 1991 and WO 92/09300 (PCT/US91/08694), herein, describe systematic synthesis and screening of peptide and other libraries of defined structure. The method used is based on a one bead one peptide approach in which a large peptide library consisting of millions of beads are screened. Each bead contains a single peptide. The authors state:

"It is clearly not enough to use a random mixture of activated amino acids in a peptide synthesis protocol, because the widely different coupling rates of different amino acids will lead to unequal representation and because each bead will contain a mixture of different peptides. Our solution was to use a 'split synthesis' approach. The first cycle consisted of distributing a pool of resin beads into separate reaction vessels each with a single amino acid, allowing the coupling reactions to go to completion, and then repooling the beads. The cycle was repeated several times to extend the peptide chain. In this fashion, each bead should contain only a single peptide species." The library of beads was screened by a staining procedure and stained beads visualized using a microscope, and removed. The structure of the peptide is obtained by a chemical analysis of the material on the single bead. Lam et al. indicate:

"Additionally, our approach has far greater potential for applying the richness of well-established peptide chemistry to synthesize libraries incorporated D-amino acids or unnatural amino acids as well as specific secondary structures including cyclic peptides. All of this can be accomplished without need to keep records of the synthetic products as our interest is focused just on those peptides which provide a strong interaction signal with the acceptor."

Dower et al., WO 91/19818 (PCT/US91/04384) describes peptide libraries expressed as fusion proteins of bacteriophage coat proteins.

Dower et al., WO 93/06121 (PCT/US92/07815) describes a method for synthesizing random oligomers and the use of identification tags to identify oligomers with desired properties.

Ellman, U.S. Pat. No. 5,288,514 describes the solid phase and combinatorial synthesis of benzodiazepine compounds on a solid support.

Huebner, U.S. Pat. No. 5,182,366 describes the controlled synthesis of peptide mixtures using mixed resins.

Several groups have focused on a combinatorial approach for the construction of peptide libraries in order to randomly screen for drug candidates. However, although a viable strategy for the identification of potential new compounds for medicinal chemists, the standard gamut of problems associated with peptide based drugs i.e. poor bio-availability, etc. must still be addressed. Combinatorial synthesis has recently been adapted for the assembly of nucleic acid, carbohydrate, and even benzodiazepine libraries.

The continued development of strategies for labelling and/or tagging materials within the libraries has greatly expedited and simplified the process of identification of active constituents within groups of diversomers. Once a potentially useful compound has been characterized from a peptide library, medicinal chemists must shift to peptidomimetic synthesis in order to convert these potentially promising peptide compounds into small organic molecules. Hence, devising a combinatorial strategy incorporating peptidomimetics could greatly simplify the drug discovery process by providing more useful libraries of small organic molecules, and may itself directly produce a drug, an unlikely accomplishment within peptide libraries.

SUMMARY OF THE INVENTION

This invention features methods of synthesizing combinatorial libraries of chemical compounds, and combinatorial libraries of chemical compounds formed by the methods of this invention. In order to devise an effective combinatorial library strategy several criteria must be considered, including: generality, the use of at least some readily available materials, the design of synthetic routes incorporating good yielding reactions, the utilization of simple methods, the incorporation of strategies to easily monitor reaction progress and assay the final compounds, and a requirement of simple or little or no purification. These requirements are met by the present invention as will be indicated below where appropriate. Further, the invention provides for the ability to generate diverse collections of molecules which may mimic the biological activity of peptides, e.g. they are peptidomimetics, while advantageously they are not digestible in the stomach as are peptides and may therefore be orally administered. Also provided are easily diversifiable compounds which contain a peptide-like backbone but maintain a rigid structure due to their molecular ring structure, e.g. the compounds are conformationally constrained, and may act as tripeptidomimetics.

A "combinatorial library" is a collection of compounds in which the compounds comprising the collection are composed of one or more types of subunits. The sub-units may be selected from natural or unnatural moieties, including dienes, dienophiles, amino acids, nucleotides, sugars, lipids, and carbohydrates. The compounds of the combinatorial library differ in one or more ways with respect to the number, order, type or types of or modifications made to one or more of the subunits comprising the compounds. Alternatively, a combinatorial library may refer to a collection of "core molecules" which vary as to the number, type or position of R or functional groups they contain and/or identity of molecules composing the core molecule, for example, a diene and/or dienophile which react to form the core molecule. The collection of compounds is generated in a systematic way. Any method of systematically generating a collection of subunits differing from each other in one or more of the ways set forth above is a combinatorial library.

A "peptidomimetic" is a compound which, at least in part, has one or more characteristics in common with a peptide. Such characteristics may include a molecular conformation similar to that of a peptide; for example, a molecular backbone structure or similar functional properties to that of a peptide, such as the ability to bind to and activate a particular cellular receptor. However, the compounds of the present invention, unlike peptides, are resistant to degradation by hydrolysis unlike, for example, peptides orally administered. Further, the compounds of the present invention may be conformationally constrained.

A "conformationally constrained molecule" is a molecule which maintains the steric relationship between at least two functional groups on the molecule. This conformational constraint may be due to the functional steric properties of a cyclic or multi-cyclic molecule. Specifically, the term means that at least two chemical groups on a core molecule will not significantly move in a rotational manner with respect to each other. This conformational constraint may be utilized to result in a symmetrical backbone analogous to a peptide backbone, however, without the rotation between the subunits of a peptide. This constrained symmetry is believed to allow for highly effective dimerization of molecular receptors. This is biologically significant, because the dimerization of receptors is believed to be an important event in the initiation of cellular signaling by molecular receptors.

An "chemical group" includes but is not limited to alkyl, alkenyl, alkynyl, alkoxy, aryl, alkylaryl, amide, thioamide, ester, amine, ether, thioether.

An "alkyl" group refers to a saturated aliphatic hydrocarbon, including straight-chain, branched-chain, and cyclic alkyl groups. Preferably, the alkyl group has 1 to 12 carbons. More preferably it is a lower alkyl of from 1 to 7 carbons, more preferably 1 to 4 carbons. The alkyl group may be substituted or unsubstituted. When substituted the substituted group(s) may be, hydroxyl, cyano, alkoxy, =O, =S, $NO_2$, $N(CH_3)_2$, amino, or SH.

An "alkenyl" group refers to an unsaturated hydrocarbon group containing at least one carbon-carbon double bond, including straight-chain, branched-chain, and cyclic groups. Preferably, the alkenyl group has 1 to 12 carbons. More preferably it is a lower alkenyl of from 1 to 7 carbons, more preferably 1 to 4 carbons. The alkenyl group may be substituted or unsubstituted. When substituted the substituted group(s) may be, hydroxyl, cyano, alkoxy, =O, =S, $NO_2$, halogen, $N(CH_3)_2$, amino, or SH.

An "alkynyl" group refers to an unsaturated hydrocarbon group containing at least one carbon-carbon triple bond, including straight-chain, branched-chain, and cyclic groups. Preferably, the alkynyl group has 1 to 12 carbons. More preferably it is a lower alkynyl of from 1 to 7 carbons, more preferably 1 to 4 carbons. The alkynyl group may be substituted or unsubstituted. When substituted the substituted group(s) may be, hydroxyl, cyano, alkoxy, =O, =S, $NO_2$, $N(CH_3)_2$, amino or SH.

An "alkoxy" group refers to an "—O—alkyl" group, where "alkyl" is defined as described above.

An "aryl" group refers to an aromatic group which has at least one ring having a conjugated pi electron system and includes carbocyclic aryl, heterocyclic aryl and biaryl groups, all of which may be optionally substituted. The preferred substituent(s) of aryl groups are halogen, trihalomethyl, hydroxyl, SH, OH, $NO_2$, amine, thioether, cyano, alkoxy, alkyl, and amino groups.

An "alkylaryl group" refers to an alkyl (as described above), covalently joined to an aryl group (as described above).

"Carbocyclic aryl groups" are groups wherein the ring atoms on the aromatic ring are all carbon atoms. The carbon atoms are optionally substituted.

"Heterocyclic aryl groups" are groups having from 1 to 3 heteroatoms as ring atoms in the aromatic ring and the remainder of the ring atoms are carbon atoms. Suitable heteroatoms include oxygen, sulfur, and nitrogen, and include furanyl, thienyl, pyridyl, pyrrolyl, N-lower alkyl pyrrolo, pyrimidyl, pyrazinyl, imidazolyl and the like, all optionally substituted.

An "amide" refers to an —C(O)—NH—R, where R is either alkyl, aryl, alklyaryl or hydrogen.

A "thioamide" refers to —C(S)—NH—R, where R is either alkyl, aryl, alklyaryl or hydrogen.

An "ester" refers to an —C(O)—OR', where R' is either alkyl, aryl, or alklyaryl.

An "amine" refers to a —N(R")R"', where R" and R"', is independently either hydrogen, alkyl, aryl, or alklyaryl, provided that R" and R"' are not both hydrogen.

An "ether" refers to R-O-R, where R is either alkyl, aryl, or alkylaryl.

A "thioether" refers to R-S-R, where R is either alkyl, aryl, or alkylaryl.

In the present invention, the reaction forming the molecules which comprise the combinatorial libraries of the invention takes place between a diene and a dienophile utilizing the Diels-Alder reaction.

A "diene" is a compound which contains at least two multiple bonds and reacts with the dienophile to form a Diels-Alder reaction product. The diene may be linear or cyclic. The simplest diene which could participate in the Diels-Alder reaction is 1,3 butadiene. The diene may contain one or more of any different number of chemical groups so long as the Diels-Alder reaction between the diene and dienophile still occurs. Such compatibility of chemical groups with the Diels-Alder reaction may be tested for by those of ordinary skill in the art.

A "dienophile" is a compound containing a multiple bond, for example, a double or triple bond which reacts with a diene. The dienophile may be identical in structure to a diene with which it is reacted. The dienophile may be linear or cyclic. The simplest dienophile which may participate in the Diels-Alder reaction is ethylene. The dienophile may contain an electron-withdrawing group such as a carbonyl, cyano or nitro group conjugated with the multiple bond. The dienophile may contain one or more of any different number of chemical groups so long as the Diels-Alder reaction between the diene and dienophile still occurs. Such compatibility of chemical groups with the Diels-Alder reaction may be tested for by those of ordinary skill in the art.

The reaction may be adapted to solid phase synthesis by appending the initial dienophile or diene to a solid support, thus simplifying purification and facilitating the common combine and separate combinatorial synthesis method, also known as split synthesis, performed with most resin, polymer, and bead bound methods.

The "Diels-Alder reaction" is a type of chemical reaction. Specifically it is an addition reaction across a pair of conjugated multiple bonds to form a ring. The reaction involves a redistribution of electrons and bonds. In one example, two double bonds disappear, two new single bonds are formed, and a double bond appears between two atoms that formerly shared a single bond. The molecules which participate in a Diels-Alder reaction are referred to as a diene and a dienophile.

A "cyclic molecule" is a molecule which has at least one chemical moiety which forms a ring. The ring may contain three atoms or more. The molecule may contain more than one cyclic moiety, the cyclic moieties may be the same or different.

A "linear molecule" does not contain a ring structure. However, the molecule may be straight or branched.

A compound produced by the reaction of a diene and a dienophile is referred to as a "Diels-Alder product". A "Diels-Alder" product suitable for further reaction in which one or more chemical groups may be added is a "core molecule". Two core molecules attached to each other are referred to as a "dimeric core molecule", three attached core molecules would be referred to as a "trimeric core molecule", n attached core molecules, wherein n is 4 or more, would be referred to as a "multimeric core molecule." Core molecules may differ from each as to the number, position and type of functional groups which they contain. Core molecules may also differ as to the specific diene and/or dienophile from which they were formed. The core molecules of the present invention sterically resemble dipeptides, however, they are bicyclic and therefore rigid, unlike peptides. Therefore, by repetition of the basic Diels-Alder reaction with the dipeptide-like core molecule which maintains the amino and carboxy termini of a true peptide, within their usual 1,6 dipeptide relationship, the assembly of peptidomimetics comprising dimer-tetrapeptide mimics, trimerhexapeptide mimics and so on may be accomplished. Conservation of the amine-carboxy termini also allow for further coupling to other substrates of choice at will; for example, acids, amines, alcohols, and other chemical moieties.

In a first embodiment the invention comprises a series of diene and dienophile reactions resulting in the generation of a combinatorial library of at least core molecules, but the process may be continued resulting in generation of combinatorial libraries of multimeric core molecules. See FIG. 1. The use of combinatorial synthesis methods as are known to those of ordinary skill in the art are employed in the invention. In a preferred embodiment the split synthesis method of combinatorial synthesis may be utilized. Furka et al., *Int. J. Peptide Prot. Res.*, Vol. 37, pp. 487–493. If n dienophiles are initially employed in the Diels-Alder reaction, these products will be pooled and then portioned into n groups, and each group will be coupled individually to the n dienes, thus producing all available combinations. Alternatively, if n dienes are initially employed in the Diels-Alder reaction, these products will be pooled and portioned into n groups, and each group will be coupled individually to n dienophiles, thus producing all available combinations. Then a subsequent Diels-Alder reaction may be performed, and the process can be repeated forming dimeric core molecules, and so on. The dienophiles and dienes may be selected from a group X which encompasses all dienophiles and dienes which will participate in the Diels-Alder reaction. Simple screening as would be routine in the art can be utilized to identify such dienes and dienophiles.

In a preferred embodiment, the use of activated esters coupled to the dienophile, particularly the $C_6F_5OH$, allows for easy assay of reaction progress and coupling efficiency by monitoring for liberation of phenol in solution. The dienophiles are readily accessible through Horner-Emmons, Wittig, or Knoevenagel reactions with virtually any aldehyde or ketone.

In another embodiment of this invention, the method of the present invention allows for synthesis of a compound, referred to as a "functionalizable core molecule". A "functionalizable core molecule" is molecule which is the product of a diene and a dienophile and to which may be added chemical groups without the need for protection or deprotection steps equal to the number of all of the functional groups added. FIGS. 4a and 4b illustrate examples of functionalizable core molecules. Generally, any diene and dienophile which contains a chemical moiety allowing for addition of at least two functional groups to the chemical moiety may be utilized. Chemical modification of the functionalizable core molecule results in the generation of a "multifunctional core molecule". The functionalizable core molecule is reacted with the same or different functional groups in three steps resulting in formation of a multifunctional core molecule which is functionally equivalent to a three subunit compound, such as a tripeptide, without the need for protection and deprotection steps. This is in contrast to typical methods of synthesis of peptides in which due to the need for protection and deprotection steps the synthesis of a trimer containing three subunits would require six to nine steps.

A "multifunctional core molecule" is comprised of a functionalizable core molecule which has been reacted with one or more functional groups, wherein the functional groups may be the same or different from each other. A multifunctional core molecule to which one functional group has been added is referred to as a "first-modified multifunctional core molecule". A multifunctional core moleccule to which two functional groups have been added is referred to as a "second-modified multifunctional core molecule". A multifunctional core moleccule to which three functional groups have been added is referred to as a "third-modified multifunctional core molecule". Examples are illustrated in FIGS. 4a and 4b. An important aspect of the multifunctional core molecules may be seen at the bottom of FIG. 4a. The rigid backbone structure may mimic the configuration of a peptide composed of D-amino acids or L-amino acids. L-amino acids are those used by living organisms, however, the L,D-amino acids of the present invention may have great utility because they may be screened for pharmacological activity which a corresponding L-amino acid might lack.

In another embodiment of this invention combinatorial libraries of multifunctional core molecules in which one or more chemical group and/or the identity of the diene and/or dienophile forming the multifunctional core molecules vary are provided.

The practical utility of the present invention is as follows: The invention is useful for, among other things, developing new drugs. The invention is also useful for rapidly generating and developing large numbers of drug candidate molecules. The invention is useful for systematically synthesizing a large number of molecules that may vary greatly in their chemical structure or composition, or that may vary in minor aspects of their chemical structure or composition. The invention is also useful for randomly generating a large number of drug candidates, and later optimizing those candidates that show the most medicinal promise.

The combinatorial libraries generated by the methods of the present invention may be screened for pharmacologically active compounds, including peptide analogs. By pharmacologically active is meant that a compound may effect the functioning of a physiological process such as signal transduction by a cellular receptor, initiation, cessation or modulation of an immune response, modulation of heart function, nervous system function, or any other organ or organ system. A pharmacologically active compound may also stimulate or inhibit the activity of a bacteria, virus, fungus, or other infectious agent. A pharmacologically active compound may modulate the effects of a disease, that is prevent or decrease the severity of or cure a disease such as cancer, diabetes, atherosclerosis, high blood pressure, Parkinson's disease and other disease states. Screening for pharmacological activity may be performed as would be known in the art.

Compounds which have been shown to be pharmacologically active compounds may be formulated for therapeutic administration as described in detail below.

The combinatorial libraries generated by the methods of the present invention may also be screened for diagnostically useful compounds. By diagnostically useful is meant that that the compound can be used to indicate the presence of a particular disease in a human or animal.

Other and further objects, features and advantages will be apparent from the following description of the presently preferred embodiments of the invention.

BRIEF DESCRIPTION OF THE DRAWINGS

FIG. 2 illustrates a representative multimeric core molecule.

FIG. 6 illustrates the assembly of dienophile substrates.

FIG. 7 illustrates the reaction of a particular diene and dienophile.

FIG. 8 illustrates the reaction of a particular diene and dienophile.

FIG. 15 illustrates the reaction of a particular diene and dienophile.

FIG. 16 illustrates a multimeric core molecule synthesis.

FIG. 18a illustrates the compound Methyl 3-(2-Pyridinyl)propionate.

FIG. 18b illustrates the compound Methyl 3-(4-Quinolinyl)propionate.

FIG. 18c illustrates the compound Methyl 3-(4-Methoxyphenyl)propionate.

FIG. 18d illustrates the compound Methyl 3-(2-Pyrazinyl)butyroate.

FIG. 18e illustrates the compound 3-(3-Furanyl)propionaldehyde.

FIG. 18f illustrates the compound 3-(2-Pyridinyl)propionaldehyde.

FIG. 18g illustrates the compound 3-(4-Quinolinyl)propionaldehyde.

FIG. 18h illustrates the compound 3-(4-Methoxyphenyl)propionaldehyde.

DETAILED DESCRIPTION OF THE INVENTION

The methods used to generate combinatorial libraries, for example the spilt synthesis method are also compatible with the combinatorial libraries of this invention. Split synthesis is carried out as follows. A first step of attaching ten different dienophiles or dienes A, B, C . . . J, to a solid support in ten separate vessels or columns. The contents of these vessels are mixed or pooled, divided into ten new different columns, and ten further parallel syntheses carried out to provide the core molecules $XA^1$, $XB^1$, $XC^1$ . . . $XJ^1$, where X is any one of the original A–J, and $A^1$, $B^1$, $C^1$ . . . $J^1$ are ten different dienes or dienophiles which may be the same or different from A–J. Of course, fewer or more than ten syntheses can be used in this second step. In the third step, the contents of the vessels are again mixed and divided into ten further columns so that the synthetic procedure can be repeated until the whole length of the desired multimeric core molecule is synthesized. In this way a series of vessels is formed at each step, differing from those in prior steps by the presence of an extra diene or dienophile.

The final ten columns in the above example (each having a variety of different polysubunits with a known subunit at their terminus) can be assayed using any standard assay format. That is, each of the ten mixtures is assayed to determine which mixture contains one or more active compounds.

Figure 1:
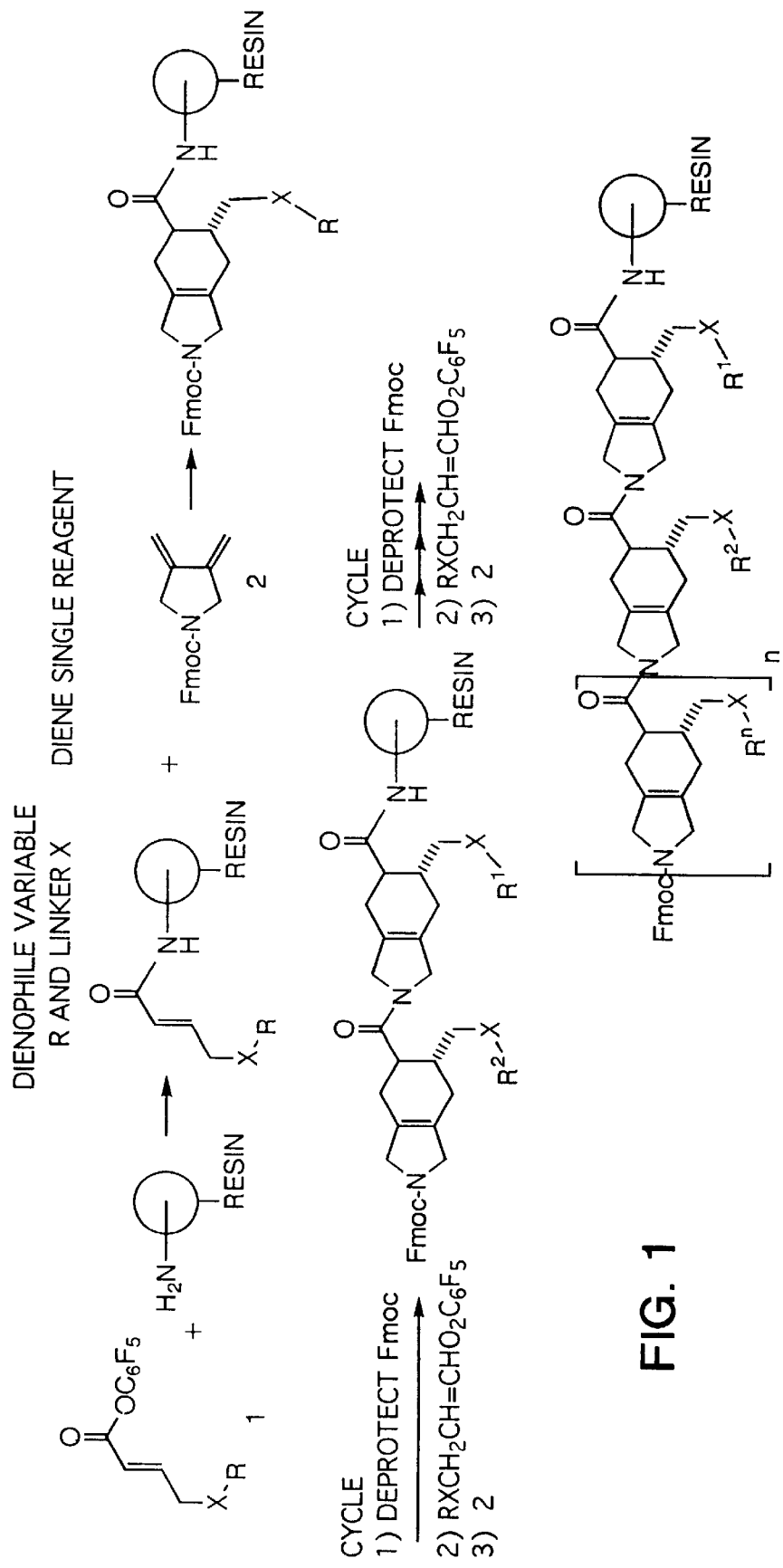
FIG. 1 illustrates the reaction of dienes and dienophiles utilizing the Diels-Alder reaction to construct multimeric core molecules which comprise the combinatorial library.
Figure 3:
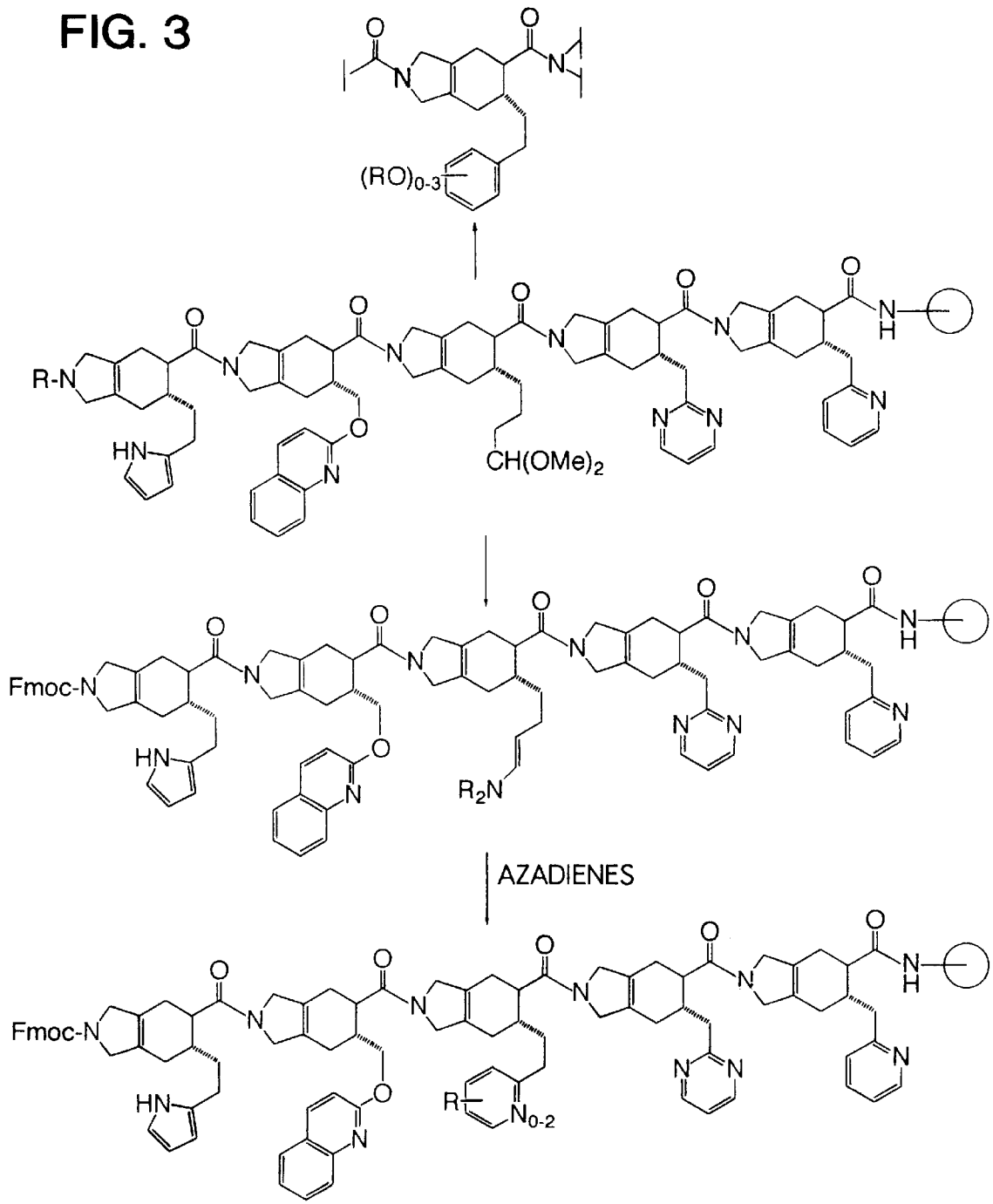
FIG. 3 illustrates a number of representative multimeric core molecules.
Figure 4A:
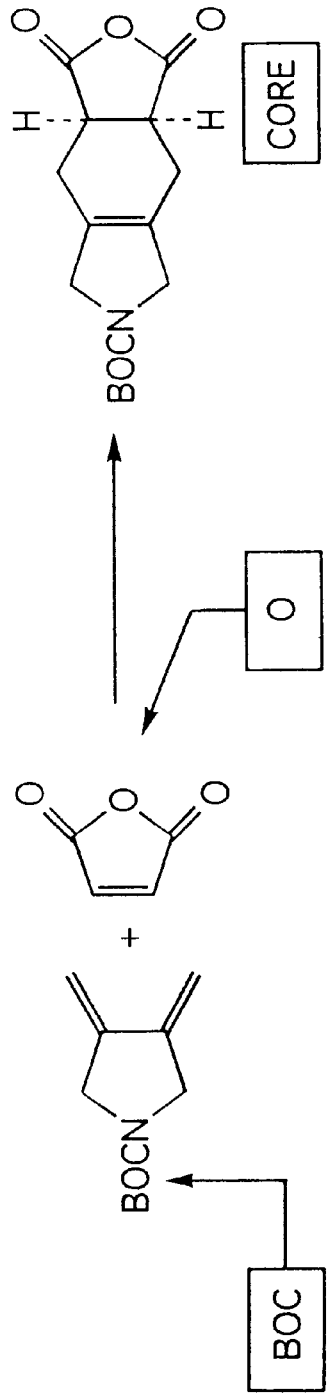
FIG. 4a illustrates the construction of a functionalizable core molecule and the generation of a multifunctional core molecule.
Figure 4B:
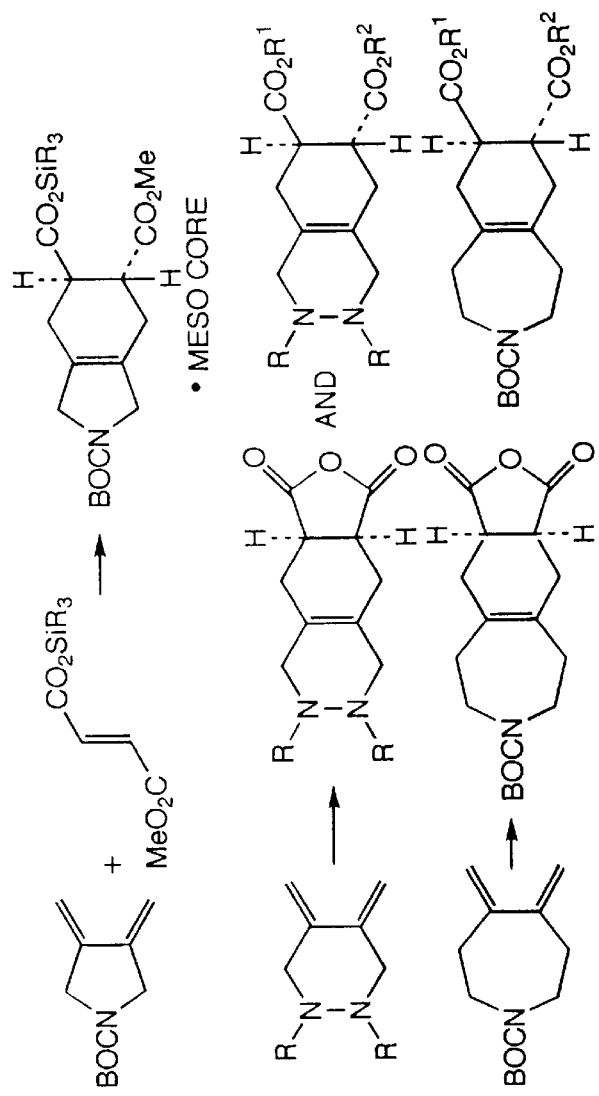
FIG. 4b illustrates several representative functionalizable core molecules.

A typical reaction sequence utilizing the method of the present invention would be carried out as follows. A resin, polymer, bead or other solid support as is known in the art may be utilized. One of n dienophiles is chemically affixed to the solid support. The dienophile may contain a linker ("X") and/or a chemical group, which may be any chemical moiety of choice, for example, one of the compounds defined above. The introduction of different substituents at the linker termini chemical group, designated R in FIG. 1, position on the dienophile allows almost limitless diversity in structure of the Diels-Alder products, FIG. 1. In a preferred embodiment, the installation of aromatics and aromatic heterocycles at this position will enhance the possibility of discovery of potential drug candidates since many medicinal agents possess these types of systems. A diene containing a protecting group, such as Fmoc is reacted with the dienophile. A first core molecule is thereby formed. The reaction should tolerate any number of protecting groups on nitrogen, as would be known to one of ordinary skill in the art and for example, BOC or Fmoc. More generally, any protecting group which does not interfere with the functional groups of the diene which participate in the Diels-Alder reaction may be utilized. The protecting group is removed and another dienophile may be reacted with the first core molecule. The second dienophile may have the same or a different linker and/or chemical group than the first dienophile. A second diene is reacted with the dienophile as above, resulting in the linkage of two core molecules and creation of a dimeric core molecule. This process may be repeated n times and will result in the creation of multimeric core molecules which may contain the same or different chemical groups. See FIGS. 2 and 3.

A typical reaction sequence to generate a multifunctional core molecule would be carried out as follows. A dienophile is reacted with a diene containing a protecting group, such as BOC. Any protecting group which does not interfere with the functional groups of the diene which participate in the Diels-Alder reaction may be used. This resulting Diels-Alder product is referred to as a functionalizable core molecule. The diene and/or dienophile may contain one or more variable chemical groups. The functionalizable core molecule may then be reacted with any alcohol, amine, thiol or other nucleophile. The resulting multifunctional core molecule may then be purified by, for example, base extraction. The multifunctional core molecule may then be reacted with any amine, alcohol, thiol or alkylating agent and then purified by, for example, acid extraction. The multifunctional core molecule may then be reacted with an acylating agent, including carboxylic acids, chloroformates, isocyanates, sulfonyl chlorides and phosphonates. The multifunctional core molecule may then be purified by, for example, acid-base extraction.

Pharmacological Compound Screening

The combinatorial libraries of the present invention may be screened for pharmacologically active compounds. Combinatorial library compounds that bind to individual cellular receptors, or functional portions of the individual cellular receptor (and may additionally be capable of disrupting receptor function) may be identified.

One such method for identifying an agent to be tested for an ability to bind to and potentially modulate a cellular receptor signal transduction pathway is as follows. The method involves exposing at least one compound from the combinatorial libraries of the present invention to a protein comprising a functional portion of a cellular receptor for a time sufficient to allow binding of the combinatorial library compound to the functional portion of the cellular receptor; removing non-bound compound; and determining the presence of the compound bound to the functional portion of the cellular receptor, thereby identifying a compound to be tested for an ability to modulate a cellular receptor signal transduction pathway.

One method utilizing this approach that may be pursued in the isolation of such receptor-binding molecules would include the attachment of a combinatorial library molecule, or a portion thereof, to a solid matrix, such as agarose or plastic beads, microtiter wells, petri dishes, or membranes composed of, for example, nylon or nitrocellulose, and the subsequent incubation of the attached combinatorial library molecule in the presence of a potential combinatorial library molecule-binding compound or compounds. Attachment to said solid support may be direct or by means of a combinatorial-library-compound-specific antibody bound directly to the solid support. After incubation, unbound compounds are washed away, component-bound compounds are recovered. By utilizing this procedure, large numbers of types of molecules may be simultaneously screened for receptor-binding activity.

Pharmaceutical Administration

When used as a therapeutic the compounds isolated from the combinatorial library of the present invention are preferably administered with a physiologically acceptable carrier. The compounds can be prepared as pharmaceutically acceptable salts (i.e., non-toxic salts which do not prevent the compound from exerting its effect).

Pharmaceutically acceptable salts can be acid addition salts such as those containing hydrochloride, sulfate, phosphate, sulfamate, acetate, citrate, lactate, tartrate, methanesulfonate, ethanesulfonate, benzenesulfonate, p-toluenesulfonate, cyclohexylsulfamate and quinate. (See, e.g., supra. PCT/US92/03736). Such salts can be derived using acids such as hydrochloric acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, and quinic acid.

Pharmaceutically acceptable salts can be prepared by standard techniques. For example, the free base form of the compound is first dissolved in a suitable solvent such as an aqueous or aqueous-alcohol solution, containing the appropriate acid. The salt is then isolated by evaporating the solution. In another example, the salt is prepared by reacting the free base and acid in an organic solvent.

Carriers or excipient can be used to facilitate administration of the compound, for example, to increase the solubility of the compound. Examples of carriers and excipients include calcium carbonate, calcium phosphate, various sugars or types of starch, cellulose derivatives, gelatin, vegetable oils, polyethylene glycols and physiologically compatible solvents. The compounds or pharmaceutical composition can be administered by different routes including intravenously, intraperitoneally, subcutaneously, and intramuscularly; orally, topically, or transmucosally.

For injection, the agents of the invention may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, many small organic molecules may be directly administered intracellularly.

Pharmaceutical compositions suitable for use in the present invention include compositions wherein the active ingredients are contained in an effective amount to achieve its intended purpose. Determination of the effective amounts is within the capability of those skilled in the art, especially in light of the detailed disclosure provided herein.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained, for example by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

For any compound used in the method of the invention, the therapeutically effective does can be estimated initially from cell culture and animal models. For example, a dose can be formulated in animal models to achieve a circulating concentration range that includes the $IC_{50}$ as determined in cell culture. Such information can be used to more accurately determine useful doses in humans.

A preferred physiological carrier is PBTE:D5W. PBTE consists of a solution of 3% w/v benzyl alcohol, 8% w/v polysorbate 80, and 65% w/v polyethylene glycol (MW=300 daltons) in absolute ethanol. PBTE:D5W consists of PBTE diluted 1:1 in a solution of 5% dextrose in water.

The use of hydrophobic compounds can be facilitated by different techniques such as combining the compound with a carrier to increase the solubility of the compound and using frequent small daily doses rather than a few large daily doses. For example, the composition can be administered at short time intervals, such as by the methods described above or using a pump to control the time interval or achieve continuous administration. Suitable pumps are commercially available (e.g., the ALZET® pump sold by Alza corporation, and the BARD ambulatory PCA pump sold by Bard MedSystems).

The proper dosage depends on various factors such as the type of disease being treated, the particular composition being used, and the size and physiological condition of the patient. Drugs can be delivered less frequently provided plasma levels of the active moiety are sufficient to maintain therapeutic effectiveness.

A factor which can influence the drug dose is body weight. Drugs should be administered at doses ranging from 0.02 to 25 mg/kg/day, preferably 0.02 to 15 mg/kg/day, most preferably 0.2 to 15 mg/kg/day. Alternatively, drugs can be administered at 0.5 to 1200 mg/m²/day, preferably 0.5 to 150 mg/m²/day, most preferably 5 to 100 mg/m²/day. The average plasma level should be 50 to 5000 µg/ml, preferably 50 to 1000 µg/ml, and most preferably 100 to 500 µg/ml. Plasma levels may be reduced if pharmacological effective concentrations of the drug are achieved at the site of interest.

Several other features of the present invention are set forth in detail below: (1) the synthesis, stability, storage, and Diels-Alder chemistry of the outer ring diene, including choice of the proper protecting group; (2) the reactivity of trans substituted α,β-unsaturated amides as dienophiles, and (3) the physical properties of multimeric core molecules (hexapeptide mimics).

EXAMPLE 1

Construction of a Diene

The diene reactant, utilized in each Diels-Alder reaction in the sequence, may be chosen to be highly reactive due to the strained locked cisoid conformation of the reactant. See Fringuelli, F.; Taticchi, A. *Dienes in the Diels-Alder Reaction* John Wiley & Sons, Inc. New York pp. 125–147 (1992), hereby incorporated by reference. The highly reactive 1,3-bis exo methylene diene is available, for example, from Trost 1,6-enyne cyclization with catalytic palladium (II) See, Trost, B. M.; Shi, Y. J., *J. Am. Chem. Soc.,* Vol. 115, p. 9421 (1994) and Trost, B. M. et al. *J. Am. Chem. Soc.,* Vol. 113, p. 636 (1991), incorporated herein by reference.

Figure 5:
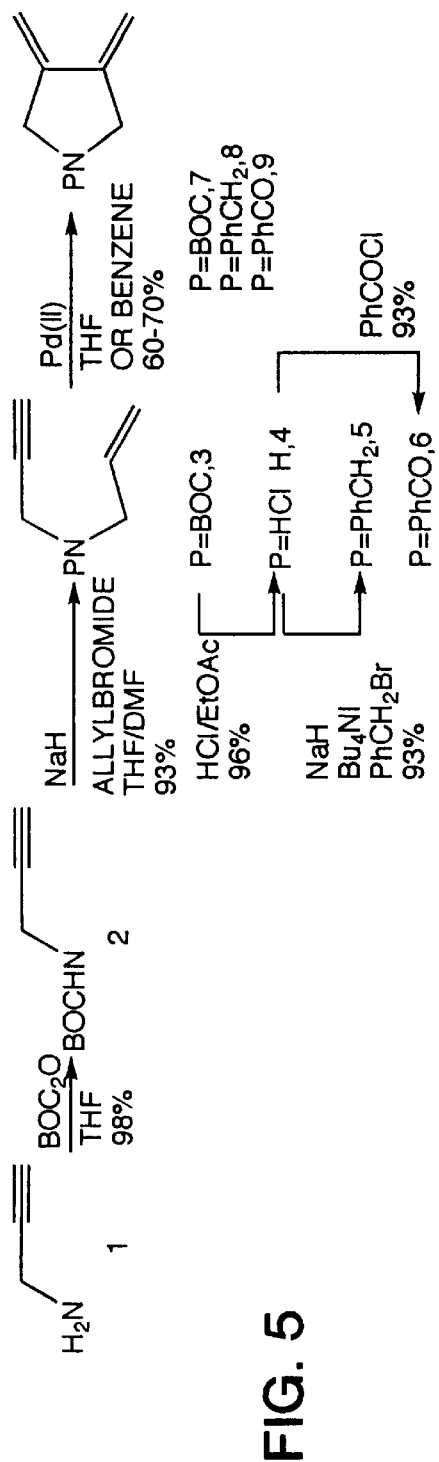
FIG. 5 illustrates the construction of a diene.
Figure 9:
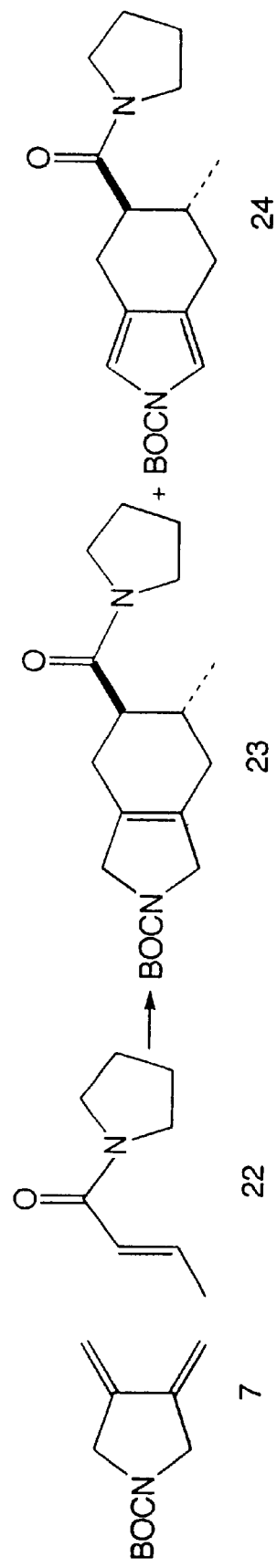
FIG. 9 illustrates the reaction of a particular diene and dienophile.
Figure 10:
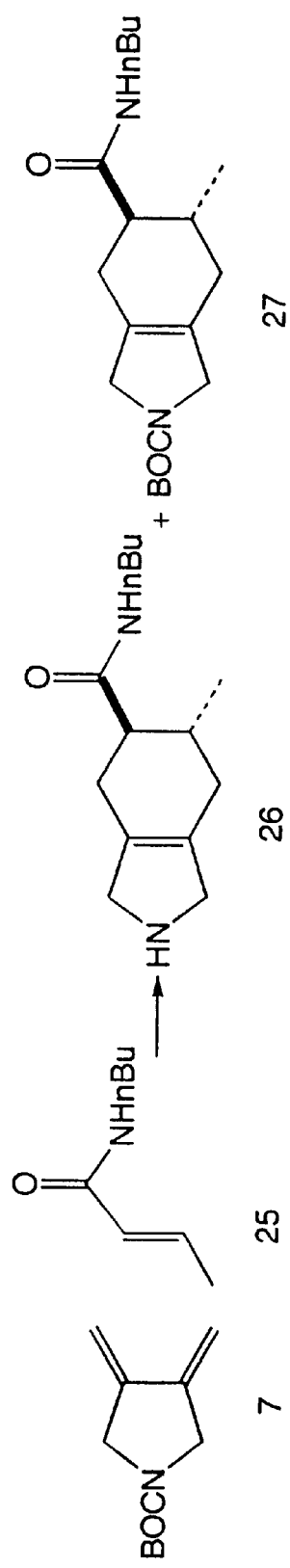
FIG. 10 illustrates the reaction of a particular diene and dienophile.
Figure 11:
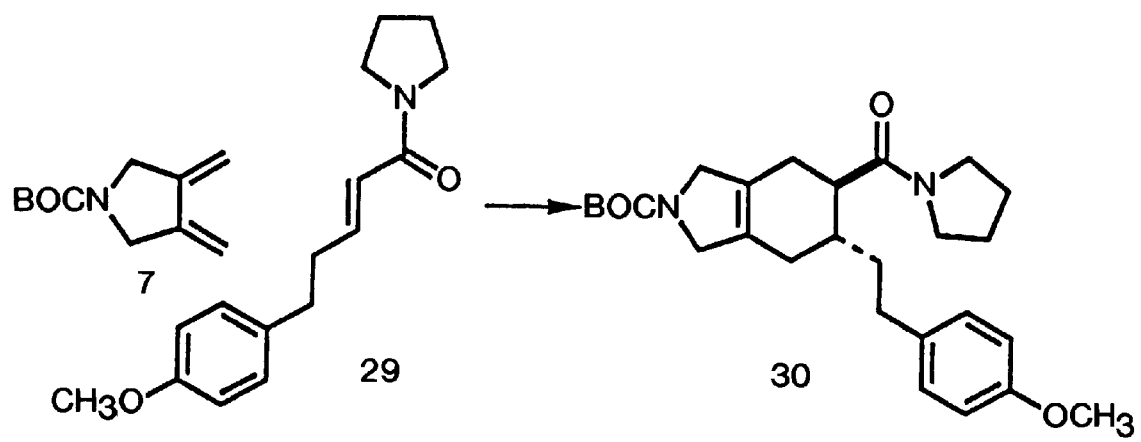
FIG. 11 illustrates the reaction of a particular diene and dienophile.

The construction of the diene was accomplished via a three step process from commercially available starting materials. As shown in FIG. 5, Scheme 2, treatment of propargyl amine, 1, with ditertbutyl dicarbonate in tetrahydrofuran (THF) furnished the NBOC material 2 in virtually quantitative yield in each instance. Alkylation of this material by reaction with sodium hydride and allyl bromide produced the enyne cyclization precursor 3 in excellent yields. The 1,6-enyne was then treated with only 5 mole % of $Pd(PPh_3)_2(OAc)_2$ in refluxing benzene or THF producing the diene 7, usually within 20 minutes, with near quantitative conversion by thin layer chromatography (tlc). Isolation and purification results in some mass loss due to oligomerization of the resulting diene upon concentration and chromatography. Once purified, the clear, colorless oil was immediately dissolved in dry benzene at 0.05M concentration under an argon atmosphere and stored in a freezer, typically around −20° C. as a frozen matrix. The isolated yield of reaction varied slightly, but 60–70% was routinely achievable on a variety of scales, 50 mg to 5 g. The enyne cyclization was also performed with different nitrogen protecting groups, particularly benzyl 5 and benzoyl 6, and the reaction remained equally successful, producing 8 and 9, respectively, as illustrated in FIG. 5.

Prior to use, the frozen diene solution 7 was allowed to warm to room temperature under an argon atmosphere, and once homogeneous was transferred via syringe, immediately sealed and placed in a freezer. The aliquot could then be quickly concentrated in vacuo at room temperature in the desired reaction vessel maintaining its integrity for further reaction.

EXAMPLE 2

Construction of a Dienophile

As illustrated in FIG. 6 Scheme 3, the assembly of dienophile substrates was carried out via a simple and general four step process applicable to almost any aldehyde 10a–d or ketone 10e, even those readily enolizable. Horner-Wittig reaction provided 11, followed by hydrogenation produced 12, DIBAL reduction furnished 13 and either Horner-Wittig or Knoevenagel reactions provided the desired dienophiles, 14 and 15 respectively. See, Popp, F. D.; Catala, A. J. *J. Org. Chem.,* Vol. 26, p. 2738 (1961), incorporated herein by reference. In some instances, the esters were reduced to the alcohols and reoxidized to the corresponding aldehydes 13. The synthesis was applied to four commercially available aldehydes (a–d) and one ketone (e) in excellent overall yield. The hydrogenation of 11a12a requires careful monitoring of the reaction conditions because excess Pd-C or extended time leads to complete hydrogenation of the furan to the tetrahydrofuran product.

EXAMPLE 3

Reactions to Yield Diels-Alder Adducts

As illustrated in FIG. 7 Scheme 4, thermolysis with simple and highly reactive dienophiles was first attempted in order to ascertain the level of reactivity for the diene 7. For instance, treatment of the just 3 equivalents of diene 7 with methyl acrylate 16, 0.3M benzene, at only 40° C. (bath) for 4–6 hours provided reproducible near quantitative yields of the Diels-Alder adduct 17. Useful to the reaction was deoxygenation of the system, rapid chromatography of the reaction mixture, and storage of the product under an argon atmosphere. Occasionally trace amounts of the pyrrole product 18 were evident from the Diels-Alder reaction directly, but the material typically appeared in greater amounts during chromatography, and even storage. If proper care in handling is observed no pyrrole oxidation product was detectable during any of the manipulations.

As illustrated in FIG. 8 Scheme 5, an acrylamide dienophile was utilized, which maintained the highly reactive monosubstituted system, while the conversion of an ester to an amide would be more similar to the type of dienophile which would more preferably be used in the present invention.

| solvent | temperature | time | results |
| --- | --- | --- | --- |
| benzene | 25–100° C. | 6 days | no rxn |
| toluene | reflux | 36 hours | 80–90% |

Simply heating 7 and 19 in benzene lead to only recovered dienophile, diene and products derived from oligomerization of the diene unit. However, changing the solvent to refluxing toluene led to excellent yielding Diels-Alder reactions, typically 80–90% yield with just 3–5 equivalents of diene. The yield of reaction may vary slightly due to the length of storage time of the diene solution, typically after prolonged periods of time the presence of oligomers is detectable. Also, but to much lesser of an extent than was found with the methyl acrylate example set forth above, the pyrrole by-product 21 could be detected, but never in greater than trace amounts.

Figure 12:
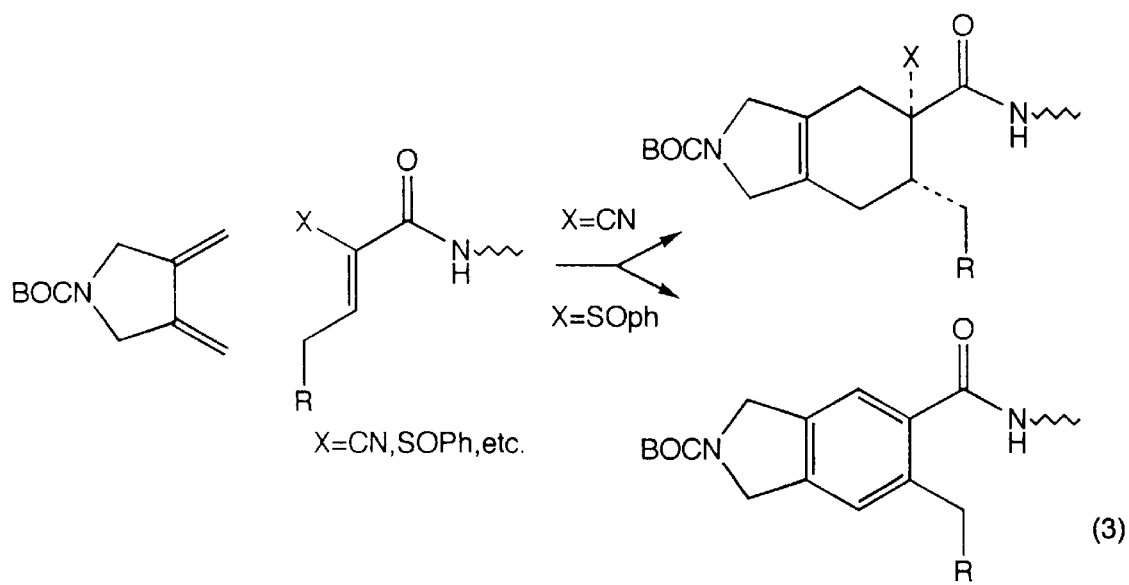
FIG. 12 illustrates the reaction of a particular diene and dienophile.

If one wants to enhance the reactivity of the dienophile several options were investigated. Stereoselective introduction of an additional electron withdrawing group, particularly a nitrile or sulfoxide, as shown in FIG. 12 was performed. The nitrile greatly enhances the dienophile reactivity, while posing little or no problem for stereoselective introduction via Knoevenagel reaction with an aldehyde or ketone, since it is such a small group, E condensation products are expected. The sulfoxide would not necessarily require stereochemical introduction, although one dienophile regioisomer may/will react faster than the other, since simple elimination followed by oxidation would provide an aromatic ring devoid of stereochemical elements.

The nitrile containing dienophiles may be preferably utilized since these Diels-Alder products will maintain the initially designed dipeptide mimics, because they avoid altering the hybridization along the backbone. These substrates are available via Knoevenagel condensation reactions of methyl cyanoacetate with the previously synthesized aldehydes. The initial compound investigated was the pyrazine, since it was the most sterically demanding dienophile, and the 4-methoxy homo cinnamate derivative since of the simple E amide dienophiles, it was the most rigorously investigated example.

Figure 13:
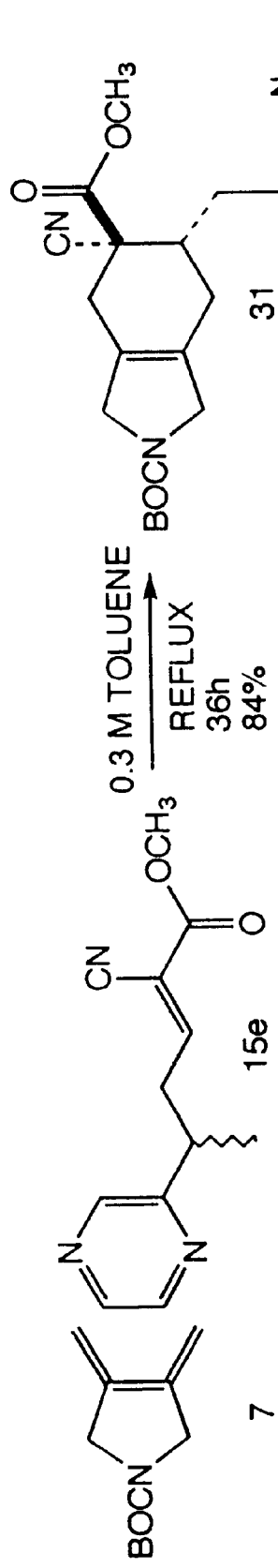
FIG. 13 illustrates the reaction of a particular diene and dienophile.

The Diels-Alder reaction between the ester/nitrile dienophile of the pyrazine substituted system 15e and 5 equivalents of the symmetrical diene 7 produced an inseparable 1:1 mixture of two diastereomers 31 in an 84% yield, see FIG. 13, Scheme 8. The introduction of the additional electron withdrawing group enhanced the reactivity of the system. Since the methyl ester of the 4-methoxy homo cinnamate derivative was so resistant in the initial Diels-Alder studies under a variety of conditions, the addition of the nitrile group to this substrate was investigated.

Figure 14:
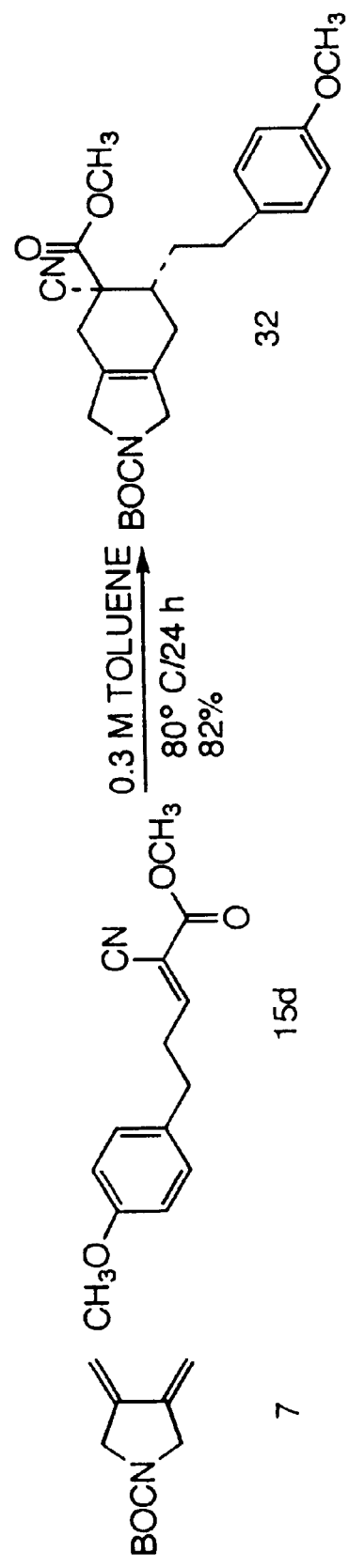
FIG. 14 illustrates the reaction of a particular diene and dienophile.

This dienophile 15d also smoothly participated in the Diels-Alder reaction with 7 in 82% yield with heating, see FIG. 14, Scheme 9. Remaining within the ultimate goals of the present invention, it remained to convert the highly reactive ester/nitrile dienophiles to amide/nitriles. Two strategies for this were pursued, (1) simple ester hydrolysis and coupling of the resulting acid to an amine and (2) the recent method developed by Roskamp for directly converting esters to amides utilizing a tin catalyst, $Sn[N(TMS)_2]_2$, Wang, W. B., Roskamp, E. J. *J. Org. Chem.* Vol. 57, 6101 (1992), incorporated herein by reference. See FIG. 15, Scheme 10.

EXAMPLE 4

Multimeric Core Molecule Synthesis

The investigation of feasibility of trimer synthesis and the study of the physical properties of these materials was carried out using the simple acrylamide dienophile 19, see FIG. 16, Scheme 11. The initial Diels-Alder reaction with the NBOC diene 7 and diethyl acrylamide 19 required thermolysis in refluxing toluene, as detailed earlier, in order to initiate reaction, 88% yield. Subsequent NBOC deprotection was accomplished with ~3.5M HCl/EtOAc 0–20° C. in 97% yield followed by coupling to acrylic acid with EDCI and HOBt provided the next dienophile 37, 87%. Diels-Alder reaction with the symmetrical diene 7 (5 equivalents) provided the Diels-Alder adduct 38 in 86% yield, accompanied by a small amount of oxidized product, pyrrole 42. After chromatography, quantitative NBOC deprotection, and coupling to acrylic acid provided the dimer dienophile 40 in 82% yield. Thermolysis of 40, in refluxing toluene for 36 hours in the presence of 5 equivalents of diene 7 provided the desired trimer product 41, 88%. This product remained soluble in standard organic solvents such as: ethyl acetate, chloroform, methylene chloride, etc, was chromatographed with conventional silica gel utilizing ethyl acetate as eluent, and possessed a low tlc $R_f$ in ethyl acetate.

EXAMPLE 5

Formation of N-[(Dimethylethoxy)carbonyl] propynyl amine (2)

Figure 17A:
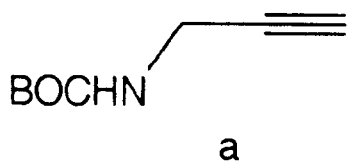
FIG. 17a illustrates the compound N-[(Dimethylethoxy)carbonyl]propynyl amine.

A solution of propargyl amine 1 (4.4 g, 79.9 mmol) in 200 mL dry THF was treated with ditertbutyl dicarbonate (17.5 g, 79.9 mmol, 18.4 mL, 1 equiv) dropwise at 0° C. (1 h) and allowed to warm to room temperature (8 h). The reaction mixture was concentrated in vacuo and recrystallized from hexanes afforded 2 (12.2 g, 12.4 g theoretical, 98%). For 2: $^1$H NMR (CDCl$_3$, 400 MHz) d 5.10–5.40 (br s, 1H, NH), 3.83 (br s, 2H, CH$_2$), 2.09 (s, 1H, C∫CH),1.39 (br s, 9H, C(CH$_3$)$_3$); $^{13}$C NMR (CDCl$_3$, 200 MHz) d 155.2, 84.8, 80.0, 79.5, 70.9, 28.0. See FIG. 17*a*.

EXAMPLE 6

Formation of N-Allyl-N-[(dimethylethoxy)carbonyl] propynyl amine (3)

Figure 17B:
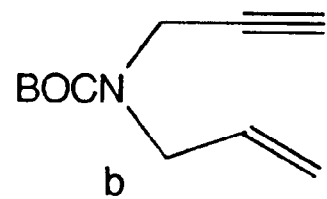
FIG. 17b illustrates the compound N-Allyl-N-[(dimethylethoxy)carbonyl]propynyl amine

A solution of 2 (10.2 g, 65.7 mmol) in 250 mL dry THF/DMF (4:1) was treated with allyl bromide (12.05 g, 98.58 mmol, 8.6 mL, 1.5 equiv) and NaH (60% oil dispersion, 3.95 g, 98.58 mmol, 1.5 equiv) at 0° C. (1 h) and allowed to warm to room temperature (6 h). The reaction mixture was concentrated in vacuo, the reside diluted with $H_2O$ (100 mL), and extracted with EtOAc (4×100 mL). The combined extracts were washed with (3×150 mL each) $H_2O$ and saturated aqueous NaCl, dried ($MgSO_4$), filtered and concentrated in vacuo. Flash chromatography ($SiO_2$, 10 cm×60 cm, 0–10% EtOAc/hexanes) afforded 3 (11.9 g, 12.83 g theoretical, 93%). For 3: $^1H$ NMR ($CDCl_3$, 250 MHz) d 5.57–5.80 (m, 1H, CH=$CH_2$), 5.10–5.25 (br m, 2H, CH=$CH_2$), 3.87–4.10 (s, 4H, $CH_2NCH_2$), 2,17 (t, 1H, J=1.9 Hz, C∫CH),1.42 (br s, 9H, C($CH_3$)$_3$); $^{13}C$ NMR ($CDCl_3$, 200 MHz) d 150.3, 133.4, 117.3, 80.4, 79.7, 71.4, 48.6, 35.4, 28.4; IR (neat) $n_{max}$ 3313, 2921, 2853, 1709, 1463, 1403, 1367, 1246, 1171, 925, 869, 770 $cm^{-1}$. See FIG. 17b.

EXAMPLE 7

Formation of 3,4-Dimethylene-N-[(dimethylethoxy)carbonyl]pyrrolidine (7)

Figure 17C:
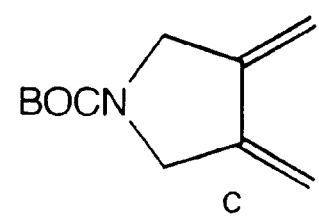
FIG. 17c illustrates the compound 3,4-Dimethylene-N-[(dimethylethoxy)carbonyl]pyrrolidine.

A solution of 3 (0.400 g, 2.05 mmol) in 50 mL dry Benzene was treated with Pd(OAc)$_2$(PPh$_3$)$_2$ (0.077 g, 0.1024 mmol, 5 mol %) at 60° C. (40 min), then concentrated in vacuo. SGC chromatotron ($SiO_2$, 2 mm, 0–30% EtOAc/hexanes) afforded 7 (0.304 g, 0.400 g theoretical, 76%). For 7: $^1H$ NMR ($C_6D_6$, 250 MHz) d 5.18 (t, 2H, J=2.5 Hz, C=CH), 4.57 (br s, 2H, C=CH), 4.14 (br s, 2H, CHC=C), 3.92 (br s, 2H, CHC=C), 1.47 (s, 9H, C($CH_3$)$_3$); IR (neat) $n_{max}$ 2925, 2853, 1703, 1403, 1252, 1169, 1114, 886, 772, 679 $cm^{-1}$. See FIG. 17c.

EXAMPLE 8

Formation of (E)-Methyl 3-(3-Furanyl)propenoate (11a)

Figure 17D:
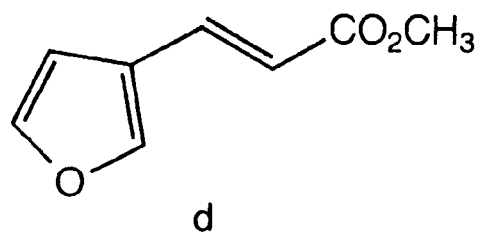
FIG. 17d illustrates the compound (E)-Methyl 3-(3-Furanyl)propenoate.

A premixed milky white heterogeneous solution of trimethylphosphono acetate (5.48 g, 30.0 mmol, 5.0 mL,, 1.2 equiv) and NaH (60% oil dispersion, 1.15 g, 28.75 mmol, 1.15 equiv) in 125 mL dry THF was stirred at 0° C. (30 min), then 3-furan carboxaldehyde 10a (2.4 g, 25.0 mmol) was added and the reaction mixture gradually became homogeneous (1 h). The reaction mixture was concentrated in vacuo, the reside diluted with $H_2O$ (75 mL), and extracted with EtOAc (3×75 mL). The combined extracts were washed with (3×100 mL each) $H_2O$ and saturated aqueous NaCl, dried ($MgSO_4$), filtered and concentrated in vacuo. SGC chromatotron ($SiO_2$, 4 mm, 0–15% EtOAc/hexanes) afforded 11a (3.61 g, 3.80 g theoretical, 95%). For 11a: $^1H$ NMR ($CDCl_3$, 250 MHz) d 7.61 (br s, 1H, Fur C2-H), 7.55 (d, 1H, J=15.8 Hz, CH=CH(C=O)), 7.39 (dd, 1H, J=1.3, 1.8 Hz, Fur C5-H), 6.55 (br d, 1H, J=1.8 Hz, Fur C4-H), 6.13 (d, 1H, J=15.8 Hz, CH(C=O)), 3.74 (s, 3H, $OCH_3$); IR (neat) $n_{max}$ 2955, 1719, 1438, 1272, 1202, 1177, 1041, 981 $cm^{-1}$. See FIG. 17d.

EXAMPLE 9

Formation of (E)-Methyl 3-(2-Pyridinyl)propenoate (11b)

Figure 17E:
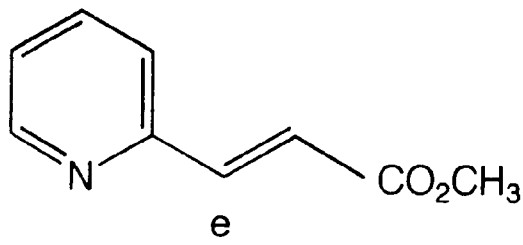
FIG. 17e illustrates the compound (E)-Methyl 3-(2-Pyridinyl)propenoate.

A premixed milky white heterogeneous solution of trimethylphosphono acetate (5.48 g, 30.0 mmol, 5.0 mL, 1.2 equiv) and NaH (60% oil dispersion, 1.15 g, 28.75 mmol, 1.15 equiv) in 125 mL dry THF was stirred at 0° C. (30 min), then 2-pyridine carboxaldehyde 10b (2.68 g, 25.0 mmol) was added and the reaction mixture gradually became homogeneous (30 min). The reaction mixture was concentrated in vacuo, the reside diluted with 75 mL $H_2O$ (75 mL), and extracted with EtOAc (3×75 mL). The combined extracts were washed with (3×100 mL each) $H_2O$ and saturated aqueous NaCl, dried ($MgSO_4$), filtered and concentrated in vacuo. SGC chromatotron ($SiO_2$, 4 mm, 0–25% EtOAc/hexanes) afforded 11b (3.97 g, 4.08 g theoretical, 97%). For 11b: $^1H$ NMR ($CDCl_3$, 400 MHz) d 8.06 (d, 1H, J=3.7 Hz, Pyr C6-H), 7.67 (ddd, 1H, J=1.8, 6.0, 7.7 Hz, Pyr C4-H), 7.54 (d, 1H, J=18.4 Hz, PyrCH=C), 7.38 (d, 1H, J=7.7 Hz, Pyr C3-H), 7.24 (dd, 1H, J=3.7, 6.0 Hz, Pyr C5-H), 6.87 (d, 1H, J=18.4 Hz, $CHCO_2CH_3$), 3.76 (s, 3H, $OCH_3$); $^{13}C$ NMR ($CDCl_{31}$ 125 MHz) d 167.0, 152.6, 149.9, 143.3, 136.6, 124.1, 123.6, 121.7, 51.6; IR (neat) $n_{max}$ 3052, 3005, 2951, 1721, 1645, 1582, 1566, 1468, 1437, 1321, 1302, 1276, 1207, 1164, 1093, 1036, 982, 934, 876, 858, 788, 746 $cm^{-1}$. See FIG. 17e.

EXAMPLE 10

Formation of (E)-Methyl 3-(4-Quinolinyl)propenoate (11c)

Figure 17F:
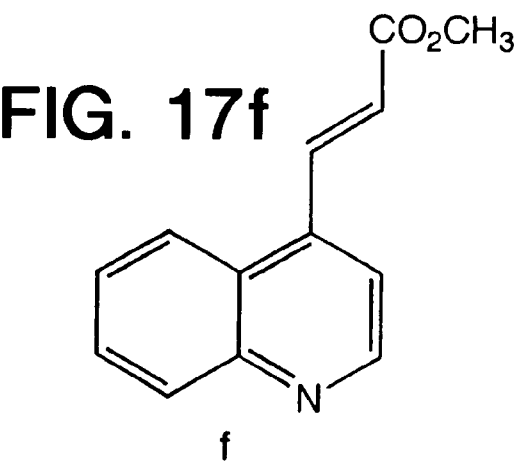
FIG. 17f illustrates the compound (E)-Methyl 3-(4-Quinolinyl)propenoate.

A premixed milky white heterogeneous solution of trimethylphosphono acetate (5.48 g, 30.0 mmol, 5.0 mL, 1.2 equiv) and NaH (60% oil dispersion, 1.15 g, 28.75 mmol, 1.15 equiv) in 125 mL dry THF was stirred at 0° C. (30 min), then 4-quinoline carboxaldehyde 10c (2.68 g, 25.0 mmol) was added and the reaction mixture gradually became homogeneous (2 h). The reaction mixture was concentrated in vacuo, the reside diluted with $H_2O$ (75 mL), and extracted with EtOAc (3×75 mL). The combined extracts were washed with (3×100 mL each) $H_2O$ and saturated aqueous NaCl, dried ($MgSO_4$), filtered and concentrated in vacuo. SGC chromatotron ($SiO_2$, 4 mm, 0–15% EtOAc/hexanes) afforded 11c (5.18 g, 5.33 g theoretical, 97%). For 11c: $^1H$ NMR ($CDCl_3$, 250 MHz) d 8.92 (d, 1H, J=4.5 Hz, Ar C2-H), 8.40 (d, 1H, J=15.9 Hz, ArCH=C), 8.15 (d, 2H, J=8.8 Hz, Ar C5-H and Ar C8-H), 7.59 (ddd, 1H, J=1.3, 7.7, 8.1 Hz, Ar C7-H), 7.61 (br dd, 1H, J=7.7, 8.1 Hz, Ar C6-H), 7.52 (d, 1H, J'4.5 Hz, Ar C3-H), 6.63 (d, 1H, J=15.9 Hz, CH(C=O)), 3.86 (s, 3H, $OCH_3$); IR (neat) $n_{max}$ 2950, 1721, 1643, 1583, 1505, 1434, 1389, 1311, 1175, 1034, 975, 842, 760 $cm^{-1}$. See FIG. 17f.

EXAMPLE 11

Formation of (E)-Methyl 3-(2-Pyrazinyl)but-2-enoate (11e)

Figure 17G:
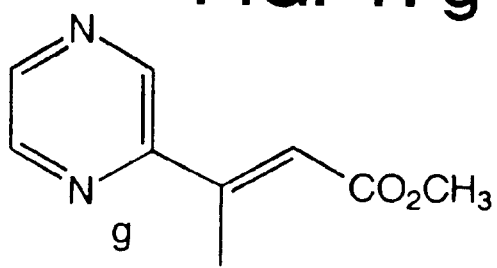
FIG. 17g illustrates the compound (E)-Methyl 3-(2-Pyrazinyl)but-2-enoate.

A premixed milky white heterogeneous solution of trimethylphosphono acetate (4.2 g, 22.6 mmol, 3.7 mL, 1.2 equiv) and NaH (60% oil dispersion, 0.859 g, 21.47 mmol, 1.15 equiv) in 110 mL dry THF was stirred at 0° C. (30 min), then 2-acetyl pyrazine 10e (2.3 g, 18.8 mmol) was added and the reaction mixture gradually became homogeneous (2 h). The reaction mixture was concentrated in vacuo, the reside diluted with $H_2O$ (75 mL) and extracted with EtOAc (3×75 mL). The combined extracts were washed with (3×100 mL each) $H_2O$ and saturated aqueous NaCl, dried ($MgSO_4$), filtered and concentrated in vacuo. SGC chromatotron ($SiO_2$, 4 mm, 20% EtOAc/hexanes) afforded 11e (2.96 g, 3.36 g theoretical, 88%). For 11e: $^1H$ NMR ($CDCl_3$, 250 MHz) d 8.51 (d, 1H, J=2.0 Hz, Pyr C5-H), 8.50 (d, 1H, J=1.6 Hz, Pyr C3-H), 8.43 (dd, 1H, J=1.6, 2.0 Hz, Pyr C6-H), 6.06 (q, 1H, J=1.6 Hz, CH(C=O)), 3.52 (s, 3H, $OCH_3$), 2.20 (s, 3H, $CH_3$); $^{13}C$ NMR ($CDCl_3$, 125 MHz) d 165.8, 154.3, 150.6, 143.9, 143.5, 143.2, 120.2, 51.3, 24.5; IR (neat) $n_{max}$ 2952, 1722, 1644, 1471, 1445, 1406, 1372, 1258, 1174, 1146, 1103, 1045, 1016, 919, 865 $cm^{-1}$. See FIG. 17g.

19

EXAMPLE 12

Formation of Methyl 3-(3-Furanyl)propionate (12a)

Figure 17H:
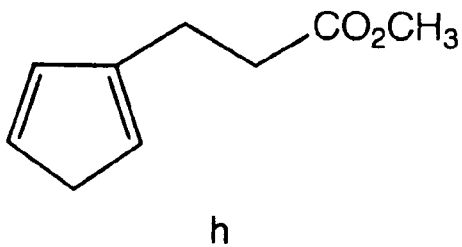
FIG. 17h illustrates the compound 3-(3-Furanyl)propionate.

A solution of 11a (2.0 g, 13.15 mmol) in 45 mL dry THF was treated with 10% Pd-C (30.0 mg, 1.5 wt %) at room temperature under a hydrogen atmosphere (balloon) (44 h). The reaction mixture was then filtered through a Celite plug, washed with EtOAc (150 mL), and concentrated in vacuo. SGC chromatotron ($SiO_2$, 4 mm, 10–20% EtOAc/hexanes) afforded 12a (1.89 g, 2.03 g theoretical, 93%). For 12a: $^1$H NMR ($CDCl_3$, 250 MHz) d 7.29 (br d, 1H, J=1.6 Hz, Fur C5-H), 7.19 (d, 1H, J=1.6 Hz, Fur C2-H), 6.22 (br s, 1H, Fur C4-H), 3.63 (s, 3H, $OCH_3$), 2.71 (t, 2H, J=7.3 Hz, $FurCH_2$), 2.52 (t, 2H, J=7.3 Hz, $CH_2(C=O)$); $^{13}$C NMR ($CDCl_3$, 125 MHz) d 173.2, 142.8, 138.9, 123.4, 110.6, 51.5, 34.4, 20.1; IR (neat) $n_{max}$ 2932, 2862, 1732, 1439, 1361, 1259, 1201, 1167, 1024, 874, 793, 731 $cm^{-1}$. See FIG. 17h.

EXAMPLE 13

Formation of Methyl 3-(2-Pyridinyl)propionate (12b)

A solution of 11b (2.0 g, 12.3 mmol) in 41 mL dry $CH_3OH$ was treated with 10% Pd-C (100.0 mg, 5 wt %) at room temperature under a hydrogen atmosphere (balloon) (10 h). The reaction mixture was then filtered through a Celite plug, washed with EtOAc (150 mL), and concentrated in vacuo. SGC chromatotron ($SiO_2$, 4 mm, 15–50% EtOAc/hexanes) afforded 12b (1.97 g, 2.03 g theoretical, 97%). For 12b: $^{-1}$H NMR ($CDCl_3$, 250 MHz) d 8.39 (d, 1H, J=2.1 Hz, Pyr C6-H), 7.46 (m, 1H, Pyr C4-H), 6.90–7.15 (br m, 2H, J=7.7 Hz, Pyr C3-H and C5-H), 3.51, 3.52, and 3.54 (three s, total 3H, $OCH_3$), 2.97 (m, 2H, $PyrCH_2$), 2.69 (m, 2H, $CH_2(C=O)$); $^{13}$C NMR ($CDCl_3$, 125 MHz) d 173.2, 159.7, 149.0, 136.1, 122.7, 121.1, 51.3, 32.8, 32.5; IR (neat) $n_{max}$ 3009, 2951, 1738, 1593, 1569, 1475, 1437, 1367, 1199, 1168, 1097, 1052, 1027, 992, 841, 755 $cm^{-1}$. See FIG. 18a.

EXAMPLE 14

Formation of Methyl 3-(4-Quinolinyl)propionate (12c)

A solution of 11c (3.14 g, 14.73 mmol) in 41 mL dry $CH_3OH$ was treated with 10% Pd-C (157.0 mg, 5 wt %) at room temperature under a hydrogen atmosphere (balloon) (8 h). The reaction mixture was then filtered through a Celite plug, washed with EtOAc (150 mL), and concentrated in vacuo. SGC chromatotron ($SiO_2$, 4 mm, 15–50% EtOAc/hexanes) afforded 12c (1.97 g, 2.03 g theoretical, 97%). For 12c: $^{-}$H NMR ($CDCl_3$, 250 MHz) d 8.77 (d, 1H, J=4.4 Hz, Ar C2-H), 8.08 (d, 1H, J=7.9 Hz, Ar C5-H or C8-H), 7.98 (d, 1H, J=7.6 Hz, Ar C5-H or Ar C8-H), 7.68 (ddd, 1H, J=1.5, 7.6, 7.9 Hz, Ar C6-H or C7-H), 7.54 (br dd, 1H, J=7.6, 7.9 Hz, Ar C6-H or C7-H), 7.21 (d, 1H, J=4.4 Hz, Ar C3-H), 3.65 (s, 3H, $OCH_3$), 3.38 (t, 2H, J=7.7 Hz, $ArCH_2$), 2.75 (t, 2H, J=7.7 Hz, $CH_2(C=O)$); IR (neat) $n_{max}$ 2952, 1738, 1594, 1572, 1510, 1435, 1367, 124, 1170, 1026, 848, 763 $cm^{-1}$. See FIG. 18b.

EXAMPLE 15

Formation of Methyl 3-(4-Methoxyphenyl) propionate (12d)

A solution of 11d (1.80 g, 9.365 mmol) in 35 mL dry THF was treated with 10% Pd-C (45.0 mg, 2.5 wt %) at room temperature under a hydrogen atmosphere (balloon) (4 h).

20

The reaction mixture was then filtered through a Celite plug, washed with EtOAc (125 mL), and concentrated in vacuo provided 12d (1.78 g, 1.82 g theoretical, 98%). For 12d: $^1$H NMR ($CDCl_3$, 250 MHz) d 7.10 (d, 2H, J=8.6 Hz, Ar C2-H and C6-H), 6.81 (d, 2H, J=8.6 Hz, Ar C3-H and C5-H), 3.76 (s, 3H, $OCH_3$), 3.74 (s, 3H, $OCH_3$), 2.88 (dd, 2H, J=7.2, 8.2 Hz, $ArCH_2$), 2.72 (dd, 2H, J=7.2, 8.2 Hz, $CH_2(C=O)$); $^{13}$C NMR ($CDCl_3$, 125 MHz) d 173.4, 158.0, 132.5, 129.2, 113.9, 55.2, 51.5, 36.0, 30.1; IR (neat) $n_{max}$ $cm^{-1}$ 2998, 2951, 1735, 1612, 1514, 1438, 1364, 1300, 1247, 1178, 1108, 1035, 829 $cm^{-1}$. See FIG. 18c.

EXAMPLE 16

Formation of Methyl 3-(2-Pyrazinyl)butyroate (12e)

A solution of 11e (2.50 g, 14.03 mmol) in 50 mL dry THF was treated with 10% Pd-C (125.0 mg, 5 wt %) at room temperature under a hydrogen atmosphere (balloon) (30 min). The reaction mixture was then filtered through a Celite plug, washed with EtOAc (150 mL), and concentrated in vacuo. SGC chromatotron ($SiO_2$, 4 mm, 20–50% EtOAc/hexanes) afforded 12e (2.48 g, 2.53 g theoretical, 98%). For 12e: $^1$H NMR ($CDCl_3$, 250 MHz) d 8.42 (d, 1H, J=1.5 Hz, Pyr C3-H), 8.38 (dd, 1H, J=1.5, 2.5 Hz, Pyr C5-H), 8.31 (d, 1H, J=2.5 Hz, Pyr C6-H), 3.51 (s, 3H, $OCH_3$), 3.39 (m, 1H, J=6.5, 7.0, 8.1 Hz, ArCH), 2.80 (dd, 1H, J=8.1, 16.1 Hz, CHH), 2.54 (dd, 1H, J=6.5, 16.1 Hz, CHH), 1.24 (d, 3H, J=7.0 Hz, $CH_3$); $^{13}$C NMR ($CDCl_3$, 125 MHz) d 172.3, 159.6, 143.9, 143.8, 142.4, 51.4, 39.7, 35.2, 20.4; IR (neat) $n_{max}$ 2978, 2935, 1737, 1473, 1406, 1371, 1280, 1180, 1034, 1015, 849, 769 $cm^{-1}$. See FIG. 18d.

EXAMPLE 17

Formation of 3-(3-Furanyl)propionaldehyde (13a)

A solution of ester 12a (2.72 g, 17.64 mmol) in 50 mL EtOH-THF (3:2) was treated with $NaBH_4$ (2.04 g, 52.93 mmol, 3 equiv) and LiCl (2.29 g, 52.93 mmol, 3 equiv) at 0° C. and allowed to warm to room temperature (8 h). The reaction mixture was quenched by the addition of acetone (10 mL) and concentrated in vacuo. The residue was dissolved in $H_2O$ (75 mL) and extracted with EtOAc (3×75 mL). The combined organic extracts were washed (3×100 mL each) $H_2O$ and saturated aqueous NaCl, dried ($MgSO_4$) and concentrated in vacuo. SGC chromatotron ($SiO_2$, 4 mm, 0–50% EtOAc/hexanes) afforded the alcohol (1.87 g, 2.23 g theoretical, 84%). For the alcohol: $^1$H NMR ($CDCl_3$, 250 MHz) d 7.33 (br s, 1H, Fur C5-H), 7.21 (br s, 1H, Fur C2-H), 6.26 (br s, 1H, Fur C4-H), 3.66 (t, 2H, $CH_2OH$), 2.50 (t, 2H, J=6.5 Hz, $FurCH_2$), 2.50 (t, 2H, J=7.6 Hz, $CH_2$), 1.81 (m, 2H, J=6.5, 7.6 Hz, $CH_2$); IR (neat) $n_{max}$ 3374, 2938, 2866, 1502, 1451, 1381, 1159, 1059, 1024, 874, 778 $cm^{-1}$.

A solution of alcohol (1.80 g, 14.3 mmol) in 50 mL dry $CH_2Cl_2$ was treated with PCC (3.08 g, 14.3 mmol, 1.0 equiv) and Celite (13.7 g) at room temperature (6 h). The reaction mixture was concentrated in vacuo to approximately 5 mL, the residue was diluted with 75 mL $Et_2O$, filtered through a Celite plug, washed with $Et_2O$ (200 mL), and concentrated in vacuo. SGC chromatotron ($SiO_2$, 4 mm, 25% EtOAc/hexanes) afforded 13a (1.56 g, 1.775 g theoretical, 88%). For 13a: $^1$H NMR ($CDCl_3$, 250 MHz) d 9.78 (s, 1H, CHO), 7.33 (br s, 1H, Fur C5-H), 7.21 (br s, 1H, Fur C2-H), 6.25 (br s, 1H, Fur C4-H), 2.72 (br m, 4H, $FurCH_2CH_2$); $^{13}$C NMR ($CDCl_3$, 125 MHz) d 201.6, 143.0, 139.0, 123.9, 110.7, 43.9, 17.4; IR (neat) $n_{max}$ 2932, 2862, 1732, 1439, 1361, 1259, 1201, 1167, 1024, 874, 793, 731 $cm^{-1}$. See FIG. 18e.

EXAMPLE 18

Formation of 3-(2-Pyridinyl)propionaldehyde (13b)

A solution of ester 12b (1.21 g, 6.752 mmol) in 22 mL dry $CH_2Cl_2$ was cooled to −78° C. and treated with DIBAL (1.0M solution in dry $CH_2Cl_2$, 6.8 mL, 6.752 mmol, 1.0 equiv), then an additional 3.2 mL DIBAL (0.5 equiv) solution was added and the reaction was quenched immediately upon completion by tlc with 4.0 mL dry $CH_3OH$. The reaction mixture was diluted with 25 mL saturated aqueous sodium potassium tartrate and warmed gradually to room temperature, partitioned, and extracted with $CH_2Cl_2$ (3×25 mL). The combined extracts were washed with saturated aqueous sodium potassium tartrate (3×25 mL), dried ($MgSO_4$), filtered and concentrated in vacuo. SGC chromatotron ($SiO_2$, 4 mm, 0–10% $CH_3OH/CHCl_3$) afforded 13 b (0.885 g, 0.9126 g theoretical, 97%). For 13b: $^1H$ NMR ($CDCl_3$, 250 MHz) d 9.80 (s, 1H, CHO), 8.38 (br s, 1H, Pyr C6-H), 7.56 (br m, 1H, Pyr C4-H), 7.00–7.20 (br m, 2H, Pyr C3-H and C5-H), 2.70–3.20 (br m, 4H, $PyrCH_2CH_2$); IR (neat) $n_{max}$, 2928, 1720, 1593, 1569, 1476, 1435, 1118, 1051, 756 $cm^{-1}$. See FIG. 18f.

EXAMPLE 19

Formation of 3-(4-Quinolinyl)propionaldehyde (13c)

A solution of ester 12 c (0.67 g, 3.11 mmol) in 10 mL EtOH-THF (3:2) was treated with $NaBH_4$ (0.404 g, 9.34 mmol, 3 equiv) and LiCl (0.36 g, 9.34 mmol, 3 equiv) at 0° C. and allowed to warm to room temperature (8 h). The reaction mixture was quenched by the addition of acetone (10 mL) and concentrated in vacuo. The residue was dissolved in $H_2O$ (50 mL) and extracted with EtOAc (3×50 mL). The combined organic extracts were washed (3×100 mL each) $H_2O$ and saturated aqueous NaCl, dried ($MgSO_4$) and concentrated in vacuo. SGC chromatotron ($SiO_2$, 4 mm, 0–50% EtOAc/hexanes) afforded the alcohol (0.523 g, 0.582 g theoretical, 90%). For the alcohol: $^1H$ NMR($CDCl_3$, 250 MHz) d 8.72 (d, 1H, J=4.4 Hz, Ar C2-H), 8.05 (m, 2H, Ar C5-H and C8-H), 7.63 (m, 1H, Ar C6-H or Ar C7-H), 7.48 (m, 1H, Ar C6-H or C7-H), 7.18 (d, 1H, J=4.4 Hz, Ar C3-H), 3.70 (t, 2H, J=6.2 Hz, $CH_2OH$), 3.13 (t, 2H, J=7.6 Hz, $ArCH_2$), 1.80–2.20 (br m, 3H, $CH_2$ and OH); IR (neat) $n_{max}$ 3280, 2939, 2868, 1591, 1574, 1510, 1060, 762 $cm^{-1}$. A solution of alcohol (0.500 g, 2.67 mmol) in 6.4 mL dry DMSO was treated with $Et_3N$ (2.7 g, 26.70 mmol, 3.7 mL, 1.0 equiv) and Pyridine.$SO_3$ (1.31 g, 8.01 mmol, 3.0 equiv) in 7.0 mL dry DMSO at room temperature (12 h). The reaction mixture was concentrated in vacuo, the residue dissolved in $H_2O$ (25 mL) and washed with EtOAc (2×25 mL). Saturated aqueous $NaHCO_3$ was added until pH>7, extracted with EtOAc (3×25 mL), combined organic layers were washed (2×30 mL each) with $H_2O$ and saturated aqueous NaCl, dried ($MgSO_4$), filtered and concentrated in vacuo. SGC chromatotron ($SiO_2$, 4 mm, 0–100% EtOAc/hexanes) afforded 13c (0.469 g, 0.495 g theoretical, 95%). For 13c: $^1H$ NMR ($CDCl_3$, 250 MHz) d 9.82 (s, 1H, CHO), 8.74 (d, 1H, J=4.4 Hz, Ar C2-H), 8.08 (d, 1H, J=7.6 Hz, Ar C5-H or C8-H), 7.93 (d, 1H 7.63, J=7.9 Hz, Ar C5-H or C8-H), 7.40–7.70 (br m, 2H, Ar C6-H and Ar C7-H), 7.18 (d, 1H, J=4.4 Hz, Ar C3-H), 3.35 (t, 2H, J=7.5 Hz, $ArCH_2$), 2.89 (t, 2H, J=7.5 Hz, $CH_2(C=O)$); IR (neat) $n_{max}$ 3258, 2936, 1723, 1591, 1510, 1391, 1069, 762 $cm^{-1}$. See FIG. 18g.

EXAMPLE 20

Formation of 3-(4-Methoxyphenyl)propionaldehyde (13d)

A solution of ester 12d (0.8346 g, 4.3 mmol) in 15 mL dry $CH_2Cl_2$ was cooled to −78° C. and treated with DIBAL (1.0M solution in dry $CH_2Cl_2$, 4.3 mL, 4.3 mmol, 1.0 equiv), upon completion by tlc the reaction was quenched immediately with 4.0 mL dry $CH_3OH$. The reaction mixture was diluted with 15 mL saturated aqueous sodium potassium tartrate and warmed gradually to room temperature, partitioned, and extracted with $CH_2Cl_2$ (3×20 mL). The combined extracts were washed with saturated aqueous sodium potassium tartrate (3×25 mL), dried ($MgSO_4$), filtered and concentrated in vacuo. SGC chromatotron ($SiO_2$, 4 mm, 20–35% EtOAc/hexanes) afforded 13d (0.702 g, 0.706 g theoretical, 99%). For 13d: $^1H$ NMR ($CDCl_3$, 250 MHz) d 9.78 (d, 1H, J=1.4 Hz, CHO), 7.09 (d, 2H, J=8.6 Hz, Ar C2-H and C6-H), 6.82 (d, 2H, J=8.6 Hz, Ar C3-H and C5-H), 3.76 (s, 3H, $OCH_3$), 2.87 (dd, 2H, J=6.9, 8.3 Hz, $ArCH_2$), 2.72 (ddd, 2H, J=1.4, 6.9, 8.3 Hz, $CH_2(C=O)$); $^{13}C$ NMR ($CDCl_3$, 125 MHz) d 201.7, 158.0, 132.3, 129.1, 113.9, 55.1, 45.4, 27.2; IR (neat) $n_{max}$ 2935, 2835, 1722, 1611, 1583, 1513, 1464, 1442, 1301, 1247, 1178, 1034, 831 $cm^{-1}$. See FIG. 18h.

EXAMPLE 21

Formation of 3-(2-Pyrazinyl)butyraldehyde (13e)

Figure 19A:
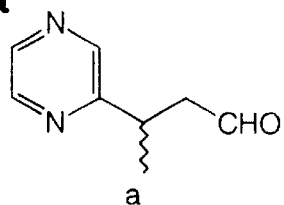
FIG. 19a illustrates the compound 3-(2-Pyrazinyl)butyraldehyde.

A solution of ester 12e (0.29 g, 1.493 mmol) in 5.3 mL dry $CH_2Cl_2$ was cooled to −78° C. and treated with DIBAL (1.0M solution in dry $CH_2Cl_2$, 1.5 mL, 1.493 mmol, 1.0 equiv), then an additional 0.7 mL DIBAL (0.5 equiv) solution was added and the reaction was quenched immediately upon completion by tlc with 2.0 mL dry $CH_3OH$. The reaction mixture was diluted with 5 mL saturated aqueous sodium potassium tartrate and warmed gradually to room temperature, partitioned, and extracted with $CH_2Cl_2$ (3×5 mL). The combined extracts were washed with saturated aqueous sodium potassium tartrate (3×5 mL), dried ($MgSO_4$), filtered and concentrated in vacuo. SGC chromatotron ($SiO_2$, 4 mm, 0–10% $CH_3OH/CHCl_3$) afforded 13e (0.213 g, 0.224 g theoretical, 95%). For 13e: $^1H$ NMR ($CDCl_3$, 250 MHz) d 9.75 (s, 1H, CHO), 8.52 (br d, 1H, J=1.5 Hz, Pyr C3-H), 8.44 (dd, 1H, J=1.5, 2.5 Hz, Pyr C5-H), 8.38 (d, 1H, J=2.5 Hz, Pyr C6-H), 3.55 (ddq, 1H, J=6.0, 7.0, 7.9 Hz, $CHCH_3$), 3.08 (ddd, 1H, J=1.2, 7.9, 17.8 Hz, CHH), 2.73 (ddd, 1H, J=1.2, 6.0, 17.8 Hz, CHH), 1.33 (d, 3H, J=7.0 Hz, $CH_3$); $^{13}C$ NMR ($CDCl_3$, 125 MHz) d 200.8, 158.2, 144.1, 143.8, 142.6, 49.3, 33.2, 20.8; IR (neat) $n_{max}$ 3054, 2966, 1722, 1668, 1525, 1471, 1406, 1294, 1147, 1117, 1016, 848, 769 $cm^{-1}$. See FIG. 19a.

EXAMPLE 22

Formation of (E)-Methyl 5-(4-Methoxyphenyl)pent-2-enoate (14d)

Figure 19B:
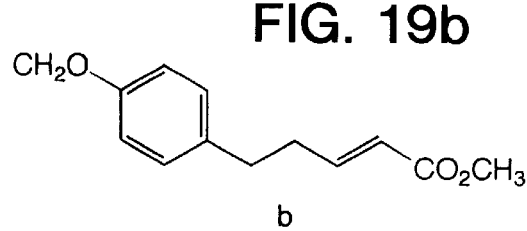
FIG. 19b illustrates the compound (E)-Methyl 5-(4-Methoxyphenyl)pent-2-enoate.

A solution of 13d (0.52 g, 3.19 mmol) in 11 mL dry Benzene was treated with $Ph_3P=CHCO_2CH_3$ (1.28 g, 3.8236 mmol, 1.2 equiv) at 60° C. (40 min), then concentrated in vacuo. SGC chromatotron ($SiO_2$, 4 mm, 0–30% EtOAc/hexanes) afforded 14d (0.625 g, 0.702 g theoretical, 89%). For 14d: $^1H$ NMR ($CDCl_3$, 250 MHz) d 7.08 (d, 2H, J=8.6 Hz, Ar C2-H and C6-H), 6.98 (dt, 1H, J=6.9, 15.7 Hz, ArCH=C), 6.81 (d, 2H, J=8.6 Hz, Ar C3-H and C5-H), 5.82 (dt, 1H, J=1.5, 15.7 Hz, CH(C=O)), 3.77 (s, 3H, $OCH_3$), 3.70 (s, 3H, $OCH_3$), 2.70 (dd, 2H, J=7.1, 8.1 Hz, $ArCH_2$), 2.47 (ddd, 2H, J=6.9, 7.1, 8.1 Hz, $CH_2(C=C)$); $^{13}C$ NMR ($CDCl_3$, 125 MHz) d 167.0, 157.9, 148.5, 132.7, 129.2, 121.3, 113.8, 55.2, 51.4, 34.1, 33.4; IR (neat) $n_{max}$ 2949, 1735, 1592, 1508, 1435, 1366, 1168, 848, 759 $cm^{-1}$. See FIG. 19b.

EXAMPLE 23

Formation of (E)-Methyl 2-Cyano-5-(4-Methoxyphenyl)pent-2-enoate (15d)

Figure 19C:
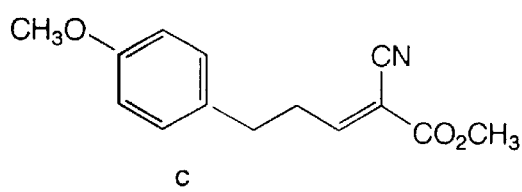
FIG. 19c illustrates the compound (E)-Methyl 2-Cyano-5-(4-Methoxyphenyl)pent-2-enoate.

A solution of 13d (0.616 g, 3.75 mmol) in 0.51 mL glacial acetic acid was treated with $NCCH_2CO_2CH_3$ (0.338 g, 3.75 mmol, 0.3 mL, 1.0 equiv), then a premixed solution of piperidine (0.0011 g, 0.128 mmol, 13 mL, 3.4 mol %) and 125 mL of acetic acid at room temperature (24 h). The reaction mixture was quenched by the addition of saturated aqueous NaHCO$_3$ (15 mL, pH>7) and extracted with EtOAc (3×15 mL). The combined organic extracts were dried (MgSO$_4$) and concentrated in vacuo. SGC chromatotron (SiO$_2$, 1 mm, 0–10% EtOAc/hexanes) afforded 15d (0.665 g, 0.920 g theoretical, 72%). For 15d: $^1$H NMR (CDCl$_3$, 400 MHz) d 7.63 (t, 1H, J=7.5 Hz, CH=C), 7.09 (d, 2H, J=8.5 Hz, Ar C2-H and C6-H), 6.83 (d, 2H, J=8.5 Hz, Ar C3-H and C5-H), 3.83 (s, 3H, OCH$_3$), 3.78 (s, 3H, OCH$_3$), 2.70–2.90 (m, 4H, ArCH$_2$CH$_2$); IR (neat) n$_{max}$ 2955, 1837, 2359, 2341, 1732, 1612, 1513, 1436, 1270, 1248, 1178, 1116, 1061, 1039, 823, 761, 668 cm$^{-1}$. See FIG. 19c.

EXAMPLE 24

Formation of (E)-Methyl 2-Cyano-5-(2-pyrazinyl) pent-2-enoate (15e)

Figure 19D:
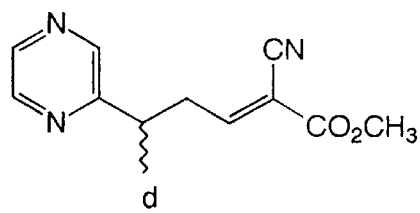
FIG. 19d illustrates the compound (E)-Methyl 2-Cyano-5-(2-pyrazinyl)pent-2-enoate.

A solution of 13e (0.191 g, 1.27 mmol) in 0.17 mL glacial acetic acid was treated with NCCH$_2$CO$_2$CH$_3$ (0.115 g, 1.27 mmol, 0.1 mL, 1.0 equiv), then a premixed solution of piperidine (0.0038 g, 0.04318 mmol, 4.4 mL, 3.4 mol %) and 50 mL of acetic acid at room temperature (24 h). The reaction mixture was quenched by the addition of saturated aqueous NaHCO$_3$ (15 mL, pH>7) and extracted with EtOAc (3×15 mL). The combined organic extracts were dried (MgSO$_4$) and concentrated in vacuo. SGC chromatotron (SiO$_2$, 1 mm, 25–65% EtOAc/hexanes) afforded 15e (0.098 g, 0.282 g theoretical, 35%). For 15e: $^1$H NMR (CDCl$_3$, 400 MHz) d 8.52 (dd, 1H, J=1.6, 2.5 Hz, Pyr C5-H), 8.46 (d, 1H, J=1.6 Hz, Pyr C3-H), 8.44 (d, 1H, J=2.5 Hz, Pyr C6-H), 7.59 (dd, 1H, J=7.8, 7.8 Hz, CH=C), 3.82 (s, 3H, OCH$_3$), 3.23 (ddq, 1H, J=6.4, 7.0, 7.2 Hz, PyrCH), 3.07 (ddd, 1H, J=7.2, 7.8, 14.9 Hz, CHH), 2.91 (ddd, 1H, J=6.4, 7.8, 14.6 Hz, CHH), 1.39 (d, 3H, J=7.0 Hz, CH$_3$); IR (neat) n$_{max}$ 2967, 2360, 2341, 1737, 1626, 1437, 1407, 1282, 1259, 1060, 1017, 850, 761, 668 cm$^-$. See FIG. 19d.

EXAMPLE 25

Formation of Methyl 2-[(Dimethylethoxy) carbonyl]-(2,3,4,5,6,7-hexahydro) isobenzazole 5-carboxylate (17)

Figure 19E:
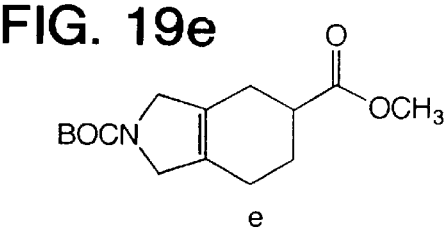
FIG. 19e illustrates the compound Methyl 2-[(Dimethylethoxy)carbonyl]-(2,3,4,5,6,7-hexahydro) isobenzazole 5-carboxylate.

A solution of 7 (0.039 g, 0.2 mmol, 3.0 equiv) in 0.2 mL toluene was treated with methyl acrylate 16 (0.0057 g, 0.0667 mmol, 6.0 mL) at 45° C. (10 h). The reaction mixture was concentrated in vacuo. SGC chromatotron (SiO$_2$, 1 mm, 0–15% EtOAc/hexanes) afforded 17 (0.0182 g, 0.0188 g theoretical, 96%). For 17: $^1$H NMR (CDCl$_3$, 400 MHz) d 3.90–4.05 (br m, 4H, C1-H$_2$ and C3-H$_2$), 3.68 (s, 3H, OCH$_3$), 2.62 (m, 1H), 2.22 (br d, 2H, J=5.8 Hz, C4-H$_2$), 2.00–2.10 (br m, 3H, C5-H and C7-H$_2$), 1.75 (br m, 1H), 1.44 (s, 9H, C(CH$_3$)$_3$); $^{13}$C NMR (CDCl$_3$, 200 MHz) d 175.7, 154.3, 129.8, 129.6, 79.2, 55.2, 55.2 (coincidental), 51.8, 39.3, 28.5, 25.5, 25.1, 22.3; IR (neat) n$_{max}$ 2974, 2849, 1737, 1708, 1687, 1403, 1366, 1343, 1256, 1225, 1167, 1109, 1014, 883, 772 cm$^{-1}$. For 18: $^1$H NMR (CDCl$_3$, 250 MHz) d 6.92 (s, 1H, C1-H or C3-H), 6.90 (s, 1H, C1-H or C3-H), 3.69 (s, 3H, OCH$_3$), 2.60–3.00 (m, 5H, C4-H$_2$, 7-C5-H, and C7-H$_2$), 2.06–2.20 (m, 1H), 1.65–1.83 (m, 1H), 1.54 (s, 9H, C(CH$_3$)$_3$); $^{13}$C NMR (CDCl$_3$, 125 MHz) d 175.9, 149.0, 122.2, 121.8, 115.3, 83.03, 51.8, 40.5, 28.0, 26.6, 24.6, 21.0; IR (neat) n$_{max}$ 2970, 1765, 1737, 1438, 1369, 1321, 1257, 1158, 1101, 939, 849, 756 cm$^{-1}$. See FIG. 19e.

EXAMPLE 26

Formation of (5R*,6R*)-n-Butyl 2-H-(2,3,4,5,6,7-hexahydro)-6-methyl-isobenzazole 5-carboxamide (26)

Figure 19F:
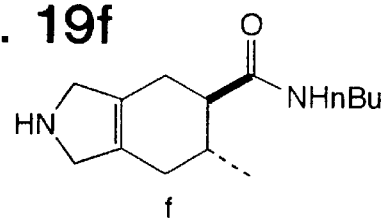
FIG. 19f illustrates the compound (5R*,6R*)-n-Butyl 2-H-(2,3,4,5,6,7-hexahydro)-6-methyl-isobenzazole 5-carboxamide.

A solution of 7 (0.100 g, 0.500 mmol, 3.0 equiv) in 0.1 mL toluene was treated with n-butyl crotonamide 25 (0.024 g, 0.167 mmol) at reflux (36 h). The reaction mixture was concentrated in vacuo. SGC chromatotron (SiO$_2$, 1 mm, 25–50% EtOAc/hexanes) afforded 26 (0.0309 g, 0.0395 g theoretical, 78%). For 26: $^1$H NMR (CDCl$_3$, 250 MHz) d 8.14 (s, 1H, NH(C=O)), 5.25–5.70 (br s, 1H, NH), 4.32–4.50 (m, 2H, C1-H$_2$ or C3-H$_2$), 3.80–4.05 (m, 2H, C1-H$_2$ or C3-H$_2$), 3.12–3.42 (br m, 4H, C4-H$_2$ and C7-H$_2$), 1.85–1.95 (m, 2H), 1.20–1.70 (br m, 9H), 0.91 (t, 3H, J=7.3 Hz, CH$_3$); IR (neat) n$_{max}$ 3419, 2964, 2924, 1766, 1699, 1479, 1393, 1260, 1197, 1098, 1020, 800, 763 cm$^{-1}$. See FIG. 19f.

EXAMPLE 27

Formation of Diethyl 2-[(Dimethylethoxy) carbonyl]-(2,3,4,5,6,7-hexahydro) isobenza-zole 5-carboxamide (20)

Figure 19G:
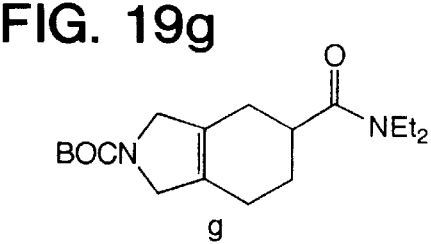
FIG. 19g illustrates the compound Diethyl 2-[(Dimethylethoxy)carbonyl]-(2,3,4,5,6,7-hexahydro) isobenza-zole 5-carboxamide.

A solution of 7 (0.300 g, 1.54 mmol, 3.0 equiv) in 0.2 mL toluene was treated with diethyl acrylamide 19 (0.0654 g, 0.513 mmol) at reflux (36 h). The reaction mixture was concentrated in vacuo. SGC chromatotron (SiO$_2$, 1 mm, 25–50% EtOAc/hexanes) afforded 20 (0.145 g, 0.165 g theoretical, 88%). For 20: $^1$H NMR (CDCl$_3$, 250 MHz) d 3.85–4.10 (br m, 4H, C1-H$_2$ and C3-H$_2$), 3.22–3.42 (br m, 4H, NCH$_2$CH$_3$), 2.68 (m, 1H), 2.22–2.42 (br m, 1H), 1.65–2.20 (br m, 5H, C4-H$_2$, C5-H and C7-H$_2$), 1.43 (s, 9H, C(CH$_3$)$_3$), 1.16 (t, 3H, J=7.1 Hz, CH$_3$), 1.08 (t, 3H, J=7.1 Hz, CH$_3$); $^{13}$C NMR (CDCl$_3$, 200 MHz) d 174.5, 154.3, 129.4, 129.4 (coincidental), 79.1, 55.5, 55.0, 41.9, 40.3, 36.7, 28.5, 26.4, 26.3, 22.8, 15.0, 13.1; IR (neat) n$_{max}$ 2972, 2932, 2848, 1708, 1687, 1640, 1403, 1259, 1164, 1109, 883, 773 cm$^{-1}$; FABHRMS (NBS-NaI) m/e 345.2162 (M+Na$^+$, C$_{18}$H$_{30}$N$_2$O$_3$ requires 345.2154). See FIG. 19g.

EXAMPLE 28

Formation of (E)-5-(4-Methoxyphenyl)pent-2-enoic Acid (28)

Figure 19H:
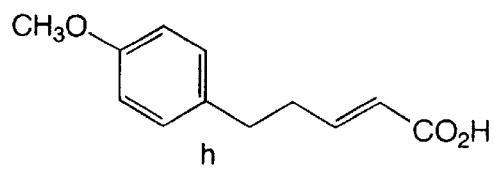
FIG. 19h illustrates the compound (E)-5-(4-Methoxyphenyl)pent-2-enoic Acid.

A solution of 14 d (1.10 g, 4.994 mmol) in 17 mL THF/CH$_3$OH/H$_2$O (3:1:1) was treated with LiOH.H$_2$O (0.63 g, 14.98 mmol, 3.0 equiv) at room temperature (6 h), then concentrated in vacuo. The resulting residue was treated with 10% aqueous HCl (~pH<3), and the white precipitate was filtered and thoroughly dried, afforded 28 (0.947 g, 1.03 g theoretical, 92%). For 28: $^1$H NMR (CD$_3$OD, 250 MHz) d 7.09 (d, 2H, J=8.5 Hz, Ar C2-H and C6-H), 6.94 (dt, 1H, J=6.9, 15.5 Hz, ArCH=C), 6.82 (d, 2H, J=8.5 Hz, Ar C3-H and C5-H), 5.76 (dd, 1H, J=1.2, 15.5 Hz, CH(C=O)), 3.74 (s, 3H, OCH$_3$), 2.70 (dd, 2H, J=7.2, 7.8 Hz, ArCH$_2$), 2.47 (ddd, 2H, J=6.9, 7.2, 7.8 Hz, CH$_2$(C=C)); $^{13}$C NMR (CD$_3$OD, 125 MHz) d 170.1, 159.5, 150.2, 134.2, 130.3, 123.0, 114.8, 55.6, 35.2, 34.5; IR (neat) n$_{max}$ 3448, 2934, 1685, 1641, 1509, 1458, 1419, 1316, 1298, 1277, 1245, 1213, 1179, 1030, 972, 820, 706 cm$^{-1}$. See FIG. 19h.

EXAMPLE 29

Formation of (E)-Pyrrolidine 5-(4-Methoxyphenyl) pent-2-enamide (29)

Figure 20A:
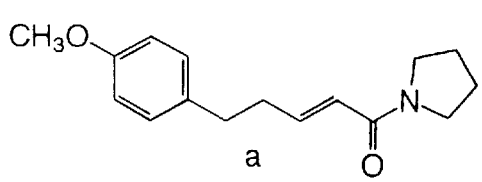
FIG. 20a illustrates the compound (E)-Pyrrolidine 5-(4-Methoxyphenyl)pent-2-enamide.

A solution of 28 (0.29 g, 1.41 mmol) in 5 mL dry CH$_2$Cl$_2$ was treated with pyrrolidine (0.502 g, 7.033 mmol, 0.6 mL, 5.0 equiv) and BOPCl (0.403 g, 1.55 mmol, 1.1 equiv) at 0–4° C. (12 h). The reaction mixture was then diluted with $CH_2Cl_2$ (10 mL) and washed with (1×10 mL each) 10% aqueous HCl, saturated aqueous $NaHCO_3$, $H_2O$ and saturated aqueous NaCl, dried ($MgSO_4$), and concentrated in vacuo. SGC chromatotron ($SiO_2$, 4 mm, 50% EtOAc/hexanes) afforded 29 (0.299 g, 0.365 g theoretical, 82%). For 29: $^1$H NMR ($CDCl_3$, 250 MHz) d 7.08 (d, 2H, J=8.6 Hz, Ar C2-H and C6-H), 6.91 (dt, 1H, J=6.9, 15.1 Hz, ArCH=C), 6.81 (d, 2H, J=8.6 Hz, Ar C3-H and C5-H), 6.06 (dd, 1H, J=1.4, 15.1 Hz, CH(C=O)), 3.76 (s, 3H, $OCH_3$), 3.46 (br m, 4H, $CH_2NCH_2$), 2.70 (apparent dd, 2H, J=7.2, 8.2 Hz, $ArCH_2$), 2.46 (apparent ddd, 2H, J=1.4, 6.9, 8.2 Hz, $CH_2(C=C)$); IR (neat) $n_{max}$ 2950, 2875, 1660, 1612, 1512, 1439, 1301, 1246, 1177, 1109, 1034, 820 $cm^{-1}$. See FIG. 20a.

EXAMPLE 30

Formation of Methyl 5a-Cyano-2-[(Dimethylethoxy)carbonyl]-(2,3,4,5,6,7-hexahydro)-6a-[2(±)-(2-pyrazinyl)propyl] isobenzazole 5b-carboxylate (31)

Figure 20B:
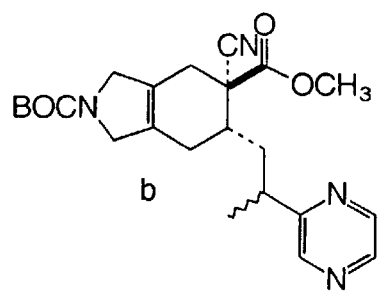
FIG. 20b illustrates the compound Methyl 5a-Cyano-2-[(Dimethylethoxy)carbonyl]-(2,3,4,5,6,7-hexahydro)-6a-[2 (±)-(2-pyrazinyl)propyl]isobenzazole 5b-carboxylate.

A solution of 7 diene (0.0409 g, 0.209 mmol, 5 equiv) in 140 mL toluene was treated with 15e (0.0092 g, 0.04184 mmol) at 80° C. (24 h). The reaction mixture was concentrated in vacuo. SGC chromatotron ($SiO_2$, 1 mm, 10–25% EtOAc/hexanes) afforded 31 (0.0143 g, 0.0175 g theoretical, 82%). For 31 (mixture of diastereomers): $^1$H NMR ($CDCl_3$, 400 MHz) d 8.49 (br s, 1H, Pyr C3-H), 8.41 (br s, 2H, Pyr C5-H and C6-H), 3.88–4.10 (br m, 4H, C1-$H_2$ and C3-$H_2$), 3.84 and 3.87 (two s, total 3H, $OCH_3$), 2.90–3.10 (m, 1H), 2.40–2.80 (br m, 2H), 2.10–2.38 (br m, 2H), 1.60–2.10 (br m, 3H), 1.43, 1.44, and 1.45 (three s, total 9H, $C(CH_3)_3$), 1.28 and 1.30 (d, total 3H, J=7.0 Hz, $CH_3$); IR (neat) $n_{max}$ 2965, 2929, 2857, 2358, 2337, 1742, 1713, 1688, 1408, 1367, 1252, 1159, 1112, 1016, 981, 882, 853, 793, 772 $cm^{-1}$. See FIG. 20b.

EXAMPLE 31

Formation of Methyl 5a-Cyano-2-[(Dimethylethoxy) carbonyl]-(2,3,4,5,6,7-hexahydro)-6a-[2-(4-methoxyphenyl)ethyl] isobenzazole 5b-carboxylate (32)

Figure 20C:
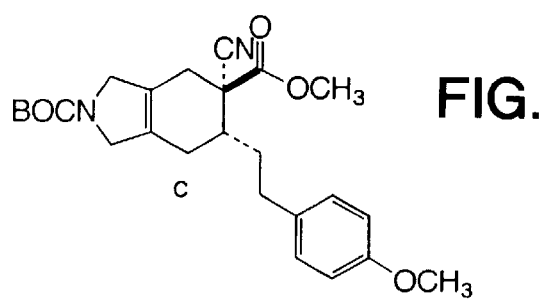
FIG. 20c illustrates the compound Methyl 5a-Cyano-2-[(Dimethylethoxy)carbonyl]-(2,3,4,5,6,7-hexahydro)-6a-[2-(4-methoxyphenyl)ethyl]isobenzazole 5b-carboxylate.

A solution of 7 diene (0.0207 g, 0.106 mmol, 5 equiv) in 70 mL toluene was treated with 15d (0.0052 g, 0.0212 mmol) at 60° C. (36 h). The reaction mixture was concentrated in vacuo. SGC chromatotron ($SiO_2$, 1 mm, 10–25% EtOAc/hexanes) afforded 32 (0.0078 g, 0.0093 g theoretical, 84%). For 32: $^1$H NMR ($CDCl_3$, 400 MHz) d 7.04 (d, 2H, J=8.6 Hz, Ar C2-H and C6-H), 6.81 (d, 2H, J=8.6 Hz, Ar C3-H and C5-H), 3.93–4.18 (br m, 4H, C1-$H_2$ and C3-$H_2$), 3.82 (s, 3H, $OCH_3$), 3.77 (s, 3H, $OCH_3$), 2.28–2.80 (br m, 5H), 2.22 (br m, 1H), 2.05 (br m, 1H), 1.71 (dt, 2H, J=7.1, 8.0 Hz, $ArCH_2CH_2$), 1.45 (s, 9H, $C(CH_3)_3$); IR (neat) $n_{max}$ 2923, 2856, 2359, 2341, 1744, 1712, 1688, 1513, 1403, 1247, 1176, 1111, 1032 $cm^{-1}$. See FIG. 20c.

EXAMPLE 32

Formation of (E)-2-Cyano-5-(4-methoxyphenyl) pent-2-enoic Acid (34)

Figure 20D:
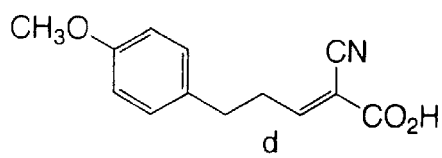
FIG. 20d illustrates the compound (E)-2-Cyano-5-(4-methoxyphenyl)pent-2-enoic Acid
Figure 20E:
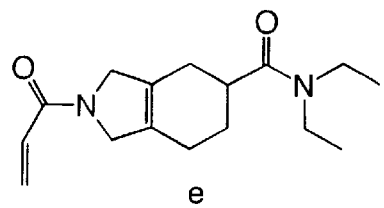
FIG. 20e illustrates the compound Diethyl 2-(1-Oxo-2-propenyl)-(2,3,4,5,6,7-hexahydro)isobenzazole 5-carboxamide.

A solution of 13e (0.0554 g, 0.2259 mmol) in 1.5 mL $THF/CH_3OH/H_2O$ (3:1:1) was treated with $LiOH.H_2O$ (0.0142 g, 0.3388 mmol, 1.5 equiv) at 0° C. (2.5 h), then concentrated in vacuo. The reside diluted with 10% aqueous HCl (10 mL) and extracted with EtOAc (3×10 mL). The combined extracts were washed with (3×10 mL each) $H_2O$ and saturated aqueous NaCl, dried ($Na_2SO_4$), filtered and concentrated in vacuo. SGC chromatotron ($SiO_2$, 1 mm, 25% EtOAc/hexanes then 0–10% $CH_3OH/CHCl_3$) afforded 33 (0.013 g, 0.042 g theoretical, 31%), 34 (0.023 g, 0.054 g theoretical, 43%), and 35 (0.003 g, 0.058 g theoretical, 5%). For 34: $^1$H NMR ($CD_3OD$, 250 MHz) d 7.20 (br s, 2H, Ar C2-H and C6-H)), 6.95 (br s, 2H, Ar C3-H and C5-H)), 3.84 (s, 3H, $OCH_3$), 2.30 (br m, 4H); IR (neat) $n_{max}$ 3444, 2965, 2929, 2359, 2342, 1714, 1702, 1679, 1408, 1367, 1255, 1111, 1015, 802, 771 $cm^{-1}$. See FIG. 20d.

EXAMPLE 33

Formation of Diethyl 2-(1-Oxo-2-propenyl)-(2,3,4,5,6,7-hexahydro)isobenzazole 5-carboxamide (37)

A solution of 20 (0.0423 g, 0.1312 mmol) in 0.2 mL dry EtOAc was treated with 3.5M HCl-EtOAc (2.0 mL) at 0° C. and immediately allowed to warm to room temperature (1 h). The reaction mixture was concentrated in vacuo and triturated with dry $Et_2O$ (3×10 mL) affording 36 (0.0329 g, 0.034 g theoretical, 97%). A solution of the amine hydrochloride salt (0.0055 g, 0.0213 mmol) in 71 mL dry DMF with EDCI (0.0124 mg, 0.0638 mmol, 3 equiv), HOBt (0.0087 g, 0.0638 mmol, 3 equiv), $NaHCO_3$ (0.0143 g, 0.017 mmol, 3 equiv), and acrylic acid (0.0016 g, 0.0213 mmol, 2 mL, 1.0 equiv) at room temperature (12 h). The reaction mixture was quenched by the addition of 10% aqueous HCl (5 mL) and extracted with EtOAc (4×5 mL). The combined extracts were washed with (3×10 mL each) saturated aqueous $NaHCO_3$, $H_2O$ and saturated aqueous NaCl, dried ($MgSO_4$), filtered and concentrated in vacuo. SGC chromatotron ($SiO_2$, 1 mm, 35–65% EtOAc/hexanes) afforded 37 (0.0051 g, 0.0059 g theoretical, 87%). For 37: $^1$H NMR ($CDCl_3$, 250 MHz) d 6.38 (dd, 1H, J=1.4, 17.3 Hz, cis-CH=CH(C=O)), 6.08 (dd, 1H, J=10.4, 17.3 Hz, trans-CH=CH(C=O)), 5.81 (dd, 1H, J=1.4, 10.4 Hz, CH(C=O)), 4.00–4.50 (br m, 4H, C1-$H_2$ and C3-$H_2$), 3.20–3.50 (br m, 4H, $NCH_2CH_3$), 2.68 (m, 1H), 2.20–2.90 (br m, 5H, C4-$H_2$, C5-H and C7-$H_2$), 1.50–2.00 (br m, 2H), 1.18 (t, 3H, J=7.0 Hz, $CH_3$), 1.11 (t, 3H, J=6.9 Hz, $CH_3$); IR (neat) $n_{max}$ 2963, 2922, 2849, 1724, 1635, 1457, 1406, 1349, 1261, 1178, 1097, 1023, 801 $cm^{-1}$. See FIG. 20c.

EXAMPLE 34

Formation of Diethyl 2-[2'-[(Dimethylethoxy) carbonyl]-(2',3',4',5',6',7'-hexahydro)isobenzazole 5'-carboxy]-(2,3,4,5,6,7-hexahydro)isobenzazole 5-carboxamide (38)

Figure 20F:
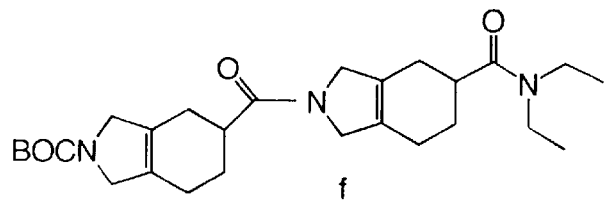
FIG. 20f illustrates the compound Diethyl 2-[2'-[(Dimethylethoxy)carbonyl]-(2',3',4',5',6',7'-hexahydro) isobenzazole 5'-carboxy]-(2,3,4,5,6,7-hexahydro) isobenzazole 5-carboxamide.

A solution of 7 diene (0.0258 g, 0.1321 mmol, 5 equiv) in 0.1 mL toluene was treated with 37 (0.0073 g, 0.0264 mmol) at reflux (36 h). The reaction mixture was concentrated in vacuo. SGC chromatotron ($SiO_2$, 1 mm, 50–75% EtOAc/hexanes) afforded 38 (0.0107 g, 0.01245 g theoretical, 86%). For 38: $^1$H NMR ($CDCl_3$, 400 MHz) d 3.85–4.20 (br m, 8H, C1'-$H_2$, C3'-$H_2$, C1-$H_2$ and C3-$H_2$), 3.25–3.50 (br m, 4H, $NCH_2CH_3$), 2.68 (m, 1H), 2.55–2.82 (br m, 3H), 2.25–2.50 (br m, 2H), 1.95–2.19 (br m, 4H), 1.60–1.95 (br m, 4H), 1.45 (s, 9H, $C(CH_3)_3$), 1.17 (t, 3H, J=7.1 Hz, $CH_3$), 1.10 (t, 3H, J=7.1 Hz, $CH_3$); IR (neat) $n_{max}$ 2969, 2929, 2847, 1708, 1687, 1639, 1632, 1432, 1402, 1365, 1258, 1163, 1107, 884 $cm^{-1}$; FABHRMS (NBS-NaI) m/e 472.3180 (M+H$^+$, $C_{27}H_{41}N_3O_4$ requires 472.3175). For 42: $^1$H NMR ($CDCl_3$, 400 MHz) d 6.92 (br s, 2H, C1'-H and C3'-H), 4.05–4.30 (br m, 4H, C1-H$_2$ and C3-H$_2$), 3.25–3.50 (br m, 4H, NCH$_2$CH$_3$), 2.30–2.87 (br m, 6H), 1.65–2.25 (br m, 8H), 1.54 (s, 9H, C(CH$_3$)$_3$), 1.05–1.30 (br m, 6H, CH$_3$); IR (neat) n$_{max}$ 2968, 2933, 2850, 1733, 1637, 1432, 1406, 1368, 1252, 1159, 975, 769 cm$^{31\ 1}$; FABHRMS (NBS) m/e 470.3015 (M+H$^+$, C$_{27}$H$_{39}$N$_3$O$_4$ requires 470.3019). See FIG. 20f.

EXAMPLE 35

Formation of Diethyl2-[2'-(1-Oxo-2-propenyl)-(2',3', 4',5',6',7'-hexahydro)-isobenzazole 5'-carboxy]-(2,3, 4,5,6,7-hexahydro)isobenzazole 5-carboxamide (40)

Figure 20G:
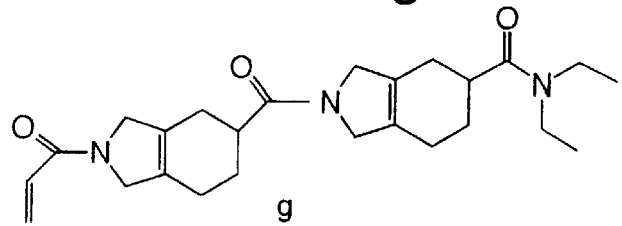
FIG. 20g illustrates the compound Diethyl 2-[2'-(1-Oxo-2-propenyl)-(2',3',4',5',6', '-hexahydro)-isobenzazole 5'-carboxy]-(2,3,4,5,6,7-hexahydro)isobenzazole 5-carboxamide.

A solution of 38 (0.0019 g, 0.004 mmol) in 0.1 mL dry EtOAc was treated with 3.5M HCl-EtOAc (0.5 mL) at 0° C. and immediately allowed to warm to room temperature (1 h). The reaction mixture was concentrated in vacuo and triturated with dry Et$_2$O (3×10 mL) affording 39 (0.0016 g, 0.0016 g theoretical, quantitative recovery). A solution of the amine hydrochloride salt (0.0017 g, 0.004 mmol) in 15 mL dry DMF with EDCI (0.0024 mg, 0.0121 mmol, 3 equiv), HOBt (0.0017 g, 0.0121 mmol, 3 equiv), NaHCO$_3$ (0.0028 g, 0.0322 mmol, 8 equiv), and acrylic acid (0.00032 g, 0.0044 mmol, 0.3 mL, 1.1 equiv) at room temperature (24 h). The reaction mixture was quenched by the addition of 10% aqueous HCl (1.5 mL) and extracted with EtOAc (4×1.5 mL). The combined extracts were washed with (2×15 mL each) saturated aqueous NaHCO$_3$, H$_2$O and saturated aqueous NaCl, dried (MgSO$_4$), filtered and concentrated in vacuo. Flash chromatography (SiO$_2$, 0.5 cm×7 cm, 50–100% EtOAc/hexanes) afforded 40 (0.0014 g, 0.0017 g theoretical, 82%). For 40: $^1$H NMR (CDCl$_3$, 250 MHz) d 6.40 (dd, 1H, J=1.5, 18.0 Hz, cis-CH=CH(C=O)), 6.00–6.20 (dd, 1H, J=10.4, 18.0 Hz, trans-CH=CH (C=O)), 5.82 (dd, 1H, J=1.5, 10.4 Hz, CH(C=O)), 4.00–4.52 (br m, 8H, C1'-H$_2$, C3'-H$_2$, C1-H$_2$ and C3-H$_2$), 3.20–3.50 (br m, 4H, NCH$_2$CH$_3$), 1.68–2.80 (br m, 14H), 1.00–1.30 (br m, 6H, CH$_3$); IR (neat) n$_{max}$ 2962, 2928, 2852, 1724, 1719, 1654, 1637, 1438, 1260, 1091, 1019, 799 cm$^{-1}$; FABHRMS (NBA) m/e 426.2750 (M+H$^+$, C$_{25}$H$_{35}$N$_3$O$_3$ requires 426.2757). See FIG. 20g.

EXAMPLE 36

Formation of Diethyl2[2'-[2"-[(Dimethylethoxy) carbonyl]-(2",3",4",5",6",7"-hexahydro)isobenzazole 5"-carboxy]-(2',3',4',5',6',7'-hexahydro)isobenzazole 5'-carboxy]-(2,3,4,5,6,7-hexahydro)isobenzazole 5-carboxamide (41)

Figure 21:
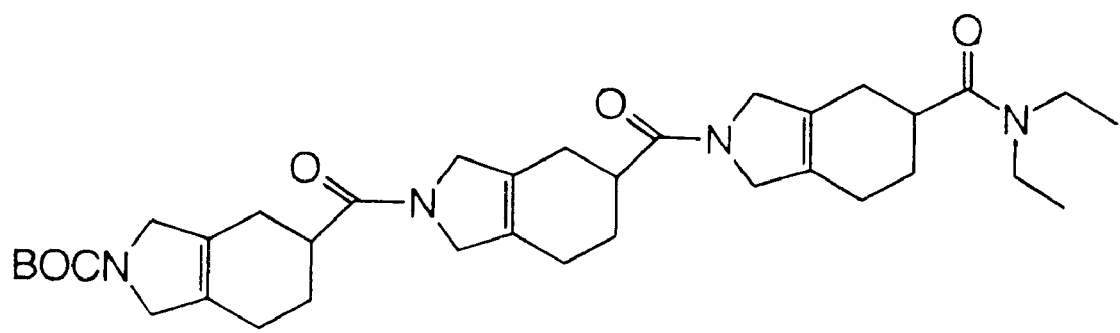
FIG. 21 illustrates the compound Diethyl 2['-[2''-[(Dimethylethoxy)carbonyl]-(2'',3'',4'',5'',6'',7''-hexahydro) isobenzazole 5''-carboxy]-(2',3',4',5',6',7'-hexahydro) isobenzazole 5'-carboxy]-(2,3,4,5,6,7-hexahydro) isobenzazole 5-carboxamide.
Figure 22:
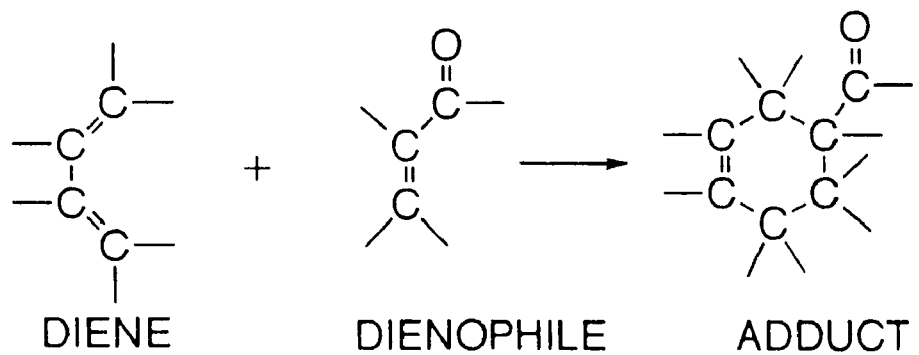
FIG. 22 illustrates a generalized Diels-Alder reaction.

A solution of 7 diene (0.0028 g, 0.0141 mmol, 5 equiv) in 10 mL toluene was treated with 40 (0.0012 g, 0.0028 mmol) at reflux (36 h). The reaction mixture was concentrated in vacuo. Flash chromatography (SiO$_2$, 0.5 cm×7.0 cm, 50–100% EtOAc/hexanes) afforded 41 (0.0107 g, 0.01245 g theoretical, 88%). For 41: $^1$H NMR (CDCl$_3$, 250 MHz) d 3.85–4.40 (br m, 12H, C1"-H$_2$, C3"-H$_2$, C1'-H$_2$, C3'-H$_2$, C1-H$_2$ and C3-H$_2$), 3.20–3.50 (br m, 4H, CH$_2$CH$_3$), 1.62–3.15 (br m, 21H), 1.44 (s, 9H, C(CH$_3$)$_3$), 1.05–1.35 (br m, 6H CH$_3$); IR (neat) n$_{max}$ 2924, 2850, 1706, 1686, 1633, 1444, 1366, 1259, 1165, 1108, 881, 806 cm$^{-1}$; FABHRMS (NBA) m/e 621.4025 (M+H$^+$, C$_{36}$H$_{52}$N$_4$O$_5$ requires 621.4016). See FIG. 21.

All patents and publications mentioned in this specification are indicative of the levels of those skilled in the art to which the invention pertains. All patents and publications are herein incorporated by reference to the same extent as if each individual publication is specifically and individually indicated to be incorporated by reference.

It will be readily apparent to one skilled in the art that various substitutions and modifications may be made to the invention disclosed herein without departing from the scope and spirit of the invention.

What is claimed is:

1. A mixture library comprising a mixture of compounds formed by reaction of one of a first through nth diene and one of a first through nth dienophile one through n times utilizing the Diels-Alder reaction, wherein n is 2 to 500.

2. The combinatorial library of claim 1 wherein at least one of said first through nth dienes comprises two multiple bonds distributed among four atoms with at least one single bond between the multiple bonds.

3. The combinatorial library of claim 1 wherein at least one of said first through nth dienophiles comprises one multiple bond distributed among two atoms.

4. The combinatorial library of claim 1 wherein at least one of said first through nth dienes is cyclic.

5. The combinatorial library of claim 1 wherein at least one of said first through nth dienes is linear.

6. The combinatorial library of claim 1 wherein at least one of said first through nth dienophiles is cyclic.

7. The combinatorial library of claim 1 wherein at least one of said first through nth dienophiles is linear.

8. The combinatorial library of claim 1 wherein said collection of compounds is generated by split synthesis.

9. A composition comprising a multifunctional core molecule formed from the reaction of a diene and a dienophile wherein said multifunctional core molecule is capable of reacting with a first chemical group without the need for a protection and deprotection step prior to addition of said first group and which upon addition of said first chemical group allows for the addition of a second chemical group without the need of a protection and deprotection step prior to addition of said second chemical group.

10. The composition of claim 9 wherein a third chemical group may be added to said core molecule.

11. A combinatorial library comprising a collection of multifunctional core molecules as in claim 10 wherein said core molecules differ from each other as to the identity of at least one of said first, second or third chemical group.

12. A combinatorial library comprising a collection of compounds formed by reaction of one of a first through nth diene and one of a first through nth dienophile one through n times utilizing the Diels-Alder reaction, wherein n is 2 to 500, wherein at least one of said first through nth dienes is selected from the group consisting of:
N-[(Dimethylethoxy)carbonyl]propynyl amine,
N-Allyl-N-[(dimethylethoxy)carbonyl]propynyl amine and
3,4-Dimethylene-N-[(dimethylethoxy)carbonyl]pyrrolidine.

13. A combinatorial library comprising a collection of compounds formed by reaction of one of a first through nth diene and one of a first through nth dienophile one through n times utilizing the Diels-Alder reaction, wherein at least one of said first through nth dienophiles is selected from the group consisting of: (E)-Methyl 3-(3-Furanyl)propenoate, (E)-Methyl 3-(2-Pyridinyl)propenoate, (E)-Methyl 3-(4-Quinolinyl)propenoate, (E)-Methyl 3-(2-Pyrazinyl)but-2-enoate, Methyl 3-(3-Furanyl)propionate, Methyl 3-(2-Pyridinyl)propionate, Methyl 3-(4-Quinolinyl)propionate, Methyl 3-(4-Methoxyphenyl)propionate, Methyl 3-(2-Pyrazinyl)butyroate, 3-(3-Furanyl)propionaldehyde, 3-(3-Furanyl)propanol, 3-(2-Pyridinyl)propionaldehyde, 3-(4-Quinolinyl)propionaldehyde, 3-(4-Quinolinyl)propanol, 3-(4-Methoxyphenyl)propionaldehyde, 3-(2-Pyrazinyl) butyraldehyde, (E)-Methyl 5-(4-Methoxyphenyl)pent-2-enoate, (E)-Methyl 2-Cyano-5-(4-Methoxyphenyl)pent-2- enoate, (E)-Methyl 2-Cyano-5-(2-pyrazinyl)pent-2-enoate, Methyl 2-[(Dimethylethoxy)carbonyl]-(2,3,4,5,6,7-hexahydro)isobenzazole 5-carboxylate, (5R*,6R*)-n-Butyl 2-H-(2,3,4,5,6,7-hexahydro)-6-methyl-isobenzazole 5-carboxamide, Diethyl 2-[(Dimethylethoxy)carbonyl]-(2,3,4,5,6,7-hexahydro)isobenzazole 5-carboxamide, (E)-5-(4-Methoxyphenyl)pent-2-enoic Acid, (E)-Pyrrolidine 5-(4-Methoxyphenyl)pent-2-enamide, Methyl 5a-Cyano-2-[(Dimethylethoxy)carbonyl]-(2,3,4,5,6,7-hexahydro)-6a-[2(±)-(2-pyrazinyl)propyl]isobenzazole 5b-carboxylate, Methyl 5a-Cyano-2-[(Dimethylethoxy)carbonyl]-(2,3,4,5,6,7-hexahydro)-6a-[2-(4-methoxyphenyl)ethyl]isobenzazole 5b-carboxylate, (E)-2-Cyano-5-(4-methoxyphenyl)pent-2-enoic Acid, Diethyl 2-(1-Oxo-2-propenyl)-(2,3,4,5,6,7-hexahydro)isobenzazole 5-carboxamide, Diethyl 2-[2'-[(Dimethylethoxy)carbonyl]-(2',3',4',5',6',7'-hexahydro)isobenzazole 5'-carboxy]-(2,3,4,5,6,7-hexahydro)isobenzazole 5-carboxamide, Diethyl 2-[2'-(1-Oxo-2-propenyl) -(2',3',4',5',6',7'-hexahydro)-isobenzazole 5'-carboxy]-(2,3,4,5,6,7-hexahydro)isobenzazole 5-carboxamide, Diethyl 2[2'-[2''-[(Dimethylethoxy)carbonyl]-(2'',3'',4'',5'',6'',7''-hexahydro)isobenzazole 5''-carboxy]-(2',3',4',5',6',7'-hexahydro)isobenzazole 5'-carboxy]-(2,3,4,5,6,7-hexahydro)isobenzazole 5-carboxamide.

14. A compound comprising the reaction product of any diene selected from the group consisting of N-[(Dimethylethoxy)carbonyl]propynyl amine, N-Allyl-N-[(dimethylethoxy)carbonyl]propynyl amine and 3,4-Dimethylene-N-[(dimethylethoxy)carbonyl]pyrrolidine reacted with any dienophile selected from the group consisting of (E)-Methyl 3-(3-Furanyl)propenoate, (E)-Methyl 3-(2-Pyridinyl)propenoate, (E)-Methyl 3-(4-Quinolinyl)propenoate, (E)-Methyl 3-(2-Pyrazinyl)but-2-enoate, Methyl 3-(3-Furanyl)propionate, Methyl 3-(2-Pyridinyl) propionate, Methyl 3-(4-Quinolinyl)propionate, Methyl 3-(4-Methoxyphenyl)propionate, Methyl 3-(2-Pyrazinyl)butyroate, 3-(3-Furanyl)propionaldehyde, 3-(3-Furanyl)propanol, 3-(2-Pyridinyl)propionaldehyde, 3-(4-Quinolinyl)propionaldehyde, 3-(4-Quinolinyl)propanol, 3-(4-Methoxyphenyl)propionaldehyde, 3-(2-Pyrazinyl)butyraldehyde, (E)-Methyl 5-(4-Methoxyphenyl)pent-2-enoate, (E)-Methyl 2-Cyano-5-(4-Methoxyphenyl)pent-2-enoate, (E)-Methyl 2-Cyano-5-(2-pyrazinyl)pent-2-enoate, Methyl 2-[(Dimethylethoxy)carbonyl]-(2,3,4,5,6,7-hexahydro)isobenzazole 5-carboxylate, (5R*,6R*)-n-Butyl 2-H-(2,3,4,5,6,7-hexahydro)-6-methyl-isobenzazole 5-carboxamide, Diethyl 2-[(Dimethylethoxy)carbonyl]-(2,3,4,5,6,7-hexahydro)isobenzazole 5-carboxamide, (E)-5-(4-Methoxyphenyl)pent-2-enoic Acid, (E)-Pyrrolidine 5-(4-Methoxyphenyl)pent-2-enamide, Methyl 5a-Cyano-2-[(Dimethylethoxy)carbonyl]-(2,3,4,5,6,7-hexahydro)-6a-[2(±)-(2-pyrazinyl)propyl]isobenzazole 5b-carboxylate, Methyl 5a-Cyano-2-[(Dimethylethoxy)carbonyl]-(2,3,4,5,6,7-hexahydro)-6a-[2-(4-methoxyphenyl)ethyl]isobenzazole 5b-carboxylate, (E)-2-Cyano-5-(4-methoxyphenyl)pent-2-enoic Acid, Diethyl 2-(1-Oxo-2-propenyl)-(2,3,4,5,6,7-hexahydro)isobenzazole 5-carboxamide, Diethyl 2-[2'-[(Dimethylethoxy)carbonyl]-(2',3',4',5',6',7'-hexahydro)isobenzazole 5'-carboxy]-(2,3,4,5,6,7-hexahydro)isobenzazole 5-carboxamide, Diethyl 2-[2'-(1-Oxo-2-propenyl)-(2',3',4',5',6',7'-hexahydro)-isobenzazole 5'-carboxy]-(2,3,4,5,6,7-hexahydro)isobenzazole 5-carboxamide, Diethyl 2[2'-[2''-[(Dimethylethoxy)carbonyl]-(2'',3'',4'',5'',6'',7''-hexahydro)isobenzazole 5''-carboxy]-(2',3',4',5',6',7'-hexahydro)isobenzazole 5'-carboxy]-(2,3,4,5,6,7-hexahydro)isobenzazole 5-carboxamide.

15. A compound comprising the reaction product of any diene selected from the group consisting of N-((Dimethylethoxy)carbonyl)propynyl amine, N-Allyl-N-((dimethylethoxy)carbonyl)propynyl amine and 3,4-Dimethylene-N-((dimethylethoxy)carbonyl)pyrrolidine; reacted with any dienophile selected from the group consisting of (E)-Methyl 3-(3-Furanyl)propenoate, (E)-Methyl 3-(2-Pyridinyl)propenoate, (E)-Methyl 3-(4-Quinolinyl)propenoate, (E)-Methyl 3-(2-Pyrazinyl)but-2-enoate, Methyl 3-(3-Furanyl)propionate, Methyl 3-(2-Pyridinyl)propionate, Methyl 3-(4-Quinolinyl)propionate, Methyl 3-(4-Methoxyphenyl)propionate, Methyl 3-(2-Pyrazinyl)butyroate, 3-(3-Furanyl)propionaldehyde, 3-(3-Furanyl)propanol, 3-(2-Pyridinyl)propionaldehyde, 3-(4-Quinolinyl)propionaldehyde, 3-(4-Quinolinyl)propanol, 3-(4-Methoxyphenyl)propionaldehyde, 3-(2-Pyrazinyl)butyraldehyde, (E)-Methyl 5-(4-Methoxyphenyl)pent-2-enoate, (E)-Methyl 2-Cyano-5-(4-Methoxyphenyl)pent-2-enoate, (E)-Methyl 2-Cyano-5-(2-pyrazinyl)pent-2-enoate, Methyl 2-((Dimethylethoxy)carbonyl)-(2,3,4, 5,6,7-hexahydro)isobenzazole 5-carboxylate, (5R*,6R*)-n-Butyl 2-H-(2,3,4,5,6,7-hexahydro)-6-methyl-isobenzazole 5-carboxamide, Diethyl 2-((Dimethylethoxy)carbonyl)-(2,3,4,5,6,7-hexahydro)isobenzazole 5-carboxamide, (E)-5-(4-Methoxyphenyl)pent-2-enoic Acid, (E)-Pyrrolidine 5-(4-Methoxyphenyl)pent-2-enamide, Methyl 5a-Cyano-2-((Dimethylethoxy)carbonyl)-(2,3,4,5,6,7-hexahydro)-6a-(2(±)-(2-pyrazinyl)propyl)isobenzazole 5b-carboxylate, Methyl 5a-Cyano-2(Dimethylethoxy)carbonyl-(2,3,4,5,6,7-hexahydro)-6a-(2-4-methoxyphenyl)ethyl)isobenzazole 5b-carboxylate, (E)-2-Cyano-5-(4-methoxyphenyl)pent-2-enoic Acid, Diethyl 2-(1-Oxo-2-propenyl)-(2,3,4,5,6,7-hexahydro)isobenzazole 5-carboxamide, Diethyl 2-(2'-((Dimethylethoxy)carbonyl) -(2',3',4',5',6',7'-hexahydro)isobenzazole 5'-carboxy)-(2,3,4,5,6,7-hexahydro)isobenzazole 5-carboxamide, Diethyl 2-(2'-(1-Oxo-2-propenyl) -(2',3',4',5',6',7'-hexahydro)-isobenzazole 5'-carboxy)-(2,3,4,5,6,7-hexahydro)isobenzazole 5-carboxamide, Diethyl 2(2'-(2''((Dimethylethoxy)carbonyl) -(2'',3'',4'',5'', 6'',7''-hexahydro)isobenzazole 5''-carboxy)-(2',3',4',5',6',7'-hexahydro)isobenzazole 5'-carboxy)-(2,3,4,5,6,7-hexahydro)isobenzazole 5-carboxamide.

* * * * *